(12) United States Patent
Roberts et al.

(10) Patent No.: US 6,458,940 B2
(45) Date of Patent: Oct. 1, 2002

(54) HPV-SPECIFIC OLIGONUCLEOTIDES

(75) Inventors: Peter C. Roberts, Holliston; Bruce L. Frank, Marlborough, both of MA (US); David E. Szymkowski, Mountain View, CA (US); John S. Mills, Farnham Common (GB); John Goodchild, Westborough, MA (US); Jia L. Wolfe, Somerville, MA (US); Robert E. Kilkuskie, Shrewsbury, MA (US); Isobel M. Greenfield; Veronica Sullivan, both of St. Albans (GB)

(73) Assignee: Hybridon, Inc., Milford, MA (US)

( * ) Notice: Subject to any disclaimer, the term of this patent is extended or adjusted under 35 U.S.C. 154(b) by 0 days.

(21) Appl. No.: 08/887,497

(22) Filed: Jul. 2, 1997

Related U.S. Application Data

(63) Continuation-in-part of application No. 08/471,974, filed on Jun. 6, 1995, now abandoned.
(60) Provisional application No. 60/021,041, filed on Jul. 2, 1996.

(51) Int. Cl.$^7$ .................. C07H 21/02; C07H 21/04; C12Q 1/68
(52) U.S. Cl. .................. 536/23.1; 536/24.3; 435/6
(58) Field of Search .................. 435/6; 536/23.1, 536/24.3, 76; 935/76, 77, 78

(56) References Cited

U.S. PATENT DOCUMENTS

| | | | | |
|---|---|---|---|---|
| 5,220,007 A | * | 6/1993 | Pederson et al. | 536/23.1 |
| 5,272,250 A | * | 12/1993 | Spielvogel et al. | 530/300 |
| 5,283,171 A | * | 2/1994 | Manos et al. | 435/5 |
| 5,527,898 A | * | 6/1996 | Bauer et al. | 536/24.3 |
| 5,550,047 A | * | 8/1996 | Mulder | 435/238 |
| 5,593,840 A | * | 1/1997 | Bhatnagar et al. | 435/6 |
| 5,639,871 A | * | 6/1997 | Bauer et al. | 536/24.31 |
| 5,652,355 A | * | 7/1997 | Metlev et al. | 536/24.5 |
| 5,795,715 A | * | 8/1998 | Livache et al. | 435/6 |

FOREIGN PATENT DOCUMENTS

| | | | |
|---|---|---|---|
| WO | WO9108313 | * | 6/1991 |
| WO | WO9320095 | * | 10/1993 |
| WO | WO9528942 | * | 11/1995 |

OTHER PUBLICATIONS

Evander et al., J. of Virological Methods 31 : 239–250 (1991).*
Agrawal et al., PNAS 86 : 7790–7794 (1989).*
Kempe et al., Nucleic Acids Research 10(21) : 6695–6714 (1982).*
Agrawal et al., PNAS 85 : 7079–7083 (1988).*
Storey et al., Nucleic Acids Research 19(15) : 4109–4114 (1991).*
Gregorie et al., J. of Clinical Microbiology 27(12) : 2660–2665 (1989).*
Sakamoto et al., Plant Molecular Biology 13 :611–614 (1989).*
Krawczyk et al., PNAS 89 :3761–3764 (1992).*

* cited by examiner

*Primary Examiner*—Ethan C. Whisenant
(74) *Attorney, Agent, or Firm*—McDonnell Boehnen Hulbert & Berghoff

(57) ABSTRACT

The present invention discloses synthetic oligonucleotides complementary to a nucleic acid spanning the translational start site of human papillomavirus gene E1, and including at least 15 nucleotides. Also disclosed are methods and kits for inhibiting the replication of HPV, for inhibiting the expression of HPV nucleic acid and protein, for detection of HPV, and for treating HPV infections.

30 Claims, 10 Drawing Sheets

HPV-SPECIFIC OLIGONUCLEOTIDES

CROSS-REFERENCE TO RELATED APPLICATION

This application is a non-provisional filing of provisional application U.S. Ser. No. 60/021,041 filed Jul. 2, 1996 which is a continuation-in-part of U.S. Ser. No. 08/471,974, filed Jun. 6, 1995 now abondoned.

BACKGROUND OF THE INVENTION

This invention relates to the human papillomavirus. More specifically, this invention relates to the inhibition, treatment, and diagnosis of human papillomavirus-associated lesions using synthetic oligonucleotides complementary to human papillomavirus nucleic acid.

Human papillomaviruses (HPV) comprise a group of at least 70 types, based on DNA sequence diversity as measured by liquid hybridization (Pfister et al. (1994) *Intervirol.* 37:143–149). These nonenveloped DNA viruses infect epithelial cells resulting in a range of lesions from benign skin and genital warts (condyloma acuminata) and epidermodysplasia verruciformis (EV) to respiratory or laryngeal papillomatosis and cervical carcinoma. Each virus type exhibits host specificity.

Several HPV types infect genital epithelia and represent the most prevalent etiologic agents of sexually transmitted viral disease. The genital HPV types can be further subdivided into "high-risk" types that are associated with the development of neoplasms, most commonly HPV-16 and HPV-18; and "low-risk" types that are rarely associated with malignancy, most commonly HPV-6 and HPV-11. The malignant types may integrate into the genome of the host cell, thereby eliminating the requirement for viral DNA replication gene products. In contrast, the benign types, most commonly HPV6 and HPV11, rely on viral proteins E1 and E2 for replication of the episomal genome.

Current treatment for HPV infection is extremely limited. There are at present no approved HPV-specific antiviral therapeutics. Management normally involves physical destruction of the wart by surgical, cryosurgical, chemical, or laser removal of infected tissue. Topical anti-metabolites such as 5-fluorouracil and podophyllum preparations have also been used. (Reichman in *Harrison's Principles of Internal Medicine*, 13th Ed. (Isselbacher et al., eds.) McGraw-Hill, Inc., NY (1993) pp. 801–803). However, reoccurrence after these procedures is common, and subsequent repetitive treatments progressively destroy healthy tissue. Interferon has so far been the only treatment with an antiviral mode of action, but its limited effectiveness restricts its use (Cowsert (1994) *Intervirol.* 37:226–230; Bornstein et al. (1993) *Obstetrics Gynecol. Sur.* 4504:252–260; Browder et al. (1992) *Ann. Pharmacother.* 26:42–45).

Two HPV types, HPV-6 and HPV-11 are commonly associated with laryngeal papillomas, or benign epithelial tumors of the larynx. Neonates may be infected with a genital papillomavirus at the time of passage through their mother's birth canal. By the age of two, papillomas will have developed, and infected juveniles will undergo multiple surgeries for removal of benign papillomas which may occlude the airway. To date there is no method of curing juvenile onset laryngeal papillomatosis. There is consequently a serious need for a specific antiviral agent to treat human papillomavirus infection.

New chemotherapeutic agents have been developed which are capable of modulating cellular and foreign gene expression (see, Zamecnik et al. (1978) *Proc. Natl. Acad. Sci.* (USA) 75:280–284). These agents, called antisense oligonucleotides, bind to target single-stranded nucleic acid molecules according to the Watson-Crick rule or to double stranded nucleic acids by the Hoogsteen rule of base pairing, and in doing so, disrupt the function of the target by one of several mechanisms: by preventing the binding of factors required for normal transcription, splicing, or translation; by triggering the enzymatic destruction of mRNA by RNase H, or by destroying the target via reactive groups attached directly to the antisense oligonucleotide.

Improved oligonucleotides have more recently been developed that have greater efficacy in inhibiting such viruses, pathogens and selective gene expression. Some of these oligonucleotides having modifications in their internucleotide linkages have been shown to be more effective than their unmodified counterparts. For example, Agrawal et al. (*Proc. Natl. Acad. Sci.* (USA) (1988) 85:7079–7083) teaches that oligonucleotide phosphorothioates and certain oligonucleotide phosphoramidates are more effective at inhibiting HIV-1 than conventional phosphodiester-linked oligodeoxynucleotides. Agrawal et al. (*Proc. Natl. Acad. Sci.* (USA) (1989) 86:7790–7794) discloses the advantage of oligonucleotide phosphorothioates in inhibiting HIV-1 in early and chronically infected cells.

In addition, chimeric oligonucleotides having more than one type of internucleotide linkage within the oligonucleotide have been developed. Pederson et al. (U.S. Pat. Nos. 5,149,797 and 5,220,007) discloses chimeric oligonucleotides having an oligonucleotide phosphodiester or oligonucleotide phosphorothioate core sequence flanked by nucleotide methylphosphonates or phosphoramidates. Agrawal et al. (WO 94/02498) discloses hybrid oligonucleotides having regions of deoxyribonucleotides and 2'-O-methyl- ribonucleotides.

A limited number of antisense oligonucleotides have been designed which inhibit the expression of HPV. For example, oligonucleotides specific for various regions of HPV E1 and E2 mRNA have been prepared (see, e.g., U.S. Pat. No. 5,364,758, WO 91/08313, WO 93/20095, and WO 95/04748).

A need still remains for the development of oligonucleotides that are capable of inhibiting the replication and expression of human papillomavirus whose uses are accompanied by a successful prognosis and low or no cellular toxicity.

SUMMARY OF THE INVENTION

The present invention provides synthetic oligonucleotides which are complementary to a nucleic acid sequence spanning the translational start site of human papillomavirus gene E1, and which includes at least 15 nucleotides.

Also provided are pharmaceutical compositions including such oligonucleotides, methods of treating, controlling, and preventing HPV infection, methods for detecting the presence of HPV in a sample, and kits for the detection of HPV in a sample.

BRIEF DESCRIPTION OF THE DRAWINGS

The foregoing and other objects of the present invention, the various features thereof, as well as the invention itself may be more fully understood from the following description, when read together with the accompanying drawings in which.

DESCRIPTION OF THE PREFERRED EMBODIMENT

With recent advances in HPV research, it is now possible to take a more directed approach toward the development of HPV antiviral compounds. Two virus encoded proteins, E1 and E2, have been shown to be essential for viral genome replication (Ustav et al. (1991) *EMBO J.*, 10:449–457; Chiang et al. (1992) *Proc. Natl. Acad. Sci.* (USA) 89:5799–5803). Most HPV types require both proteins for initiation of viral DNA replication; however, it has recently been shown that in certain in vitro experiments only E1 is required (Gopalakrishnan et al. (1994) *Proc. Natl. Acad. Sci.* (USA) 91:9597–9601).

Figure 1:
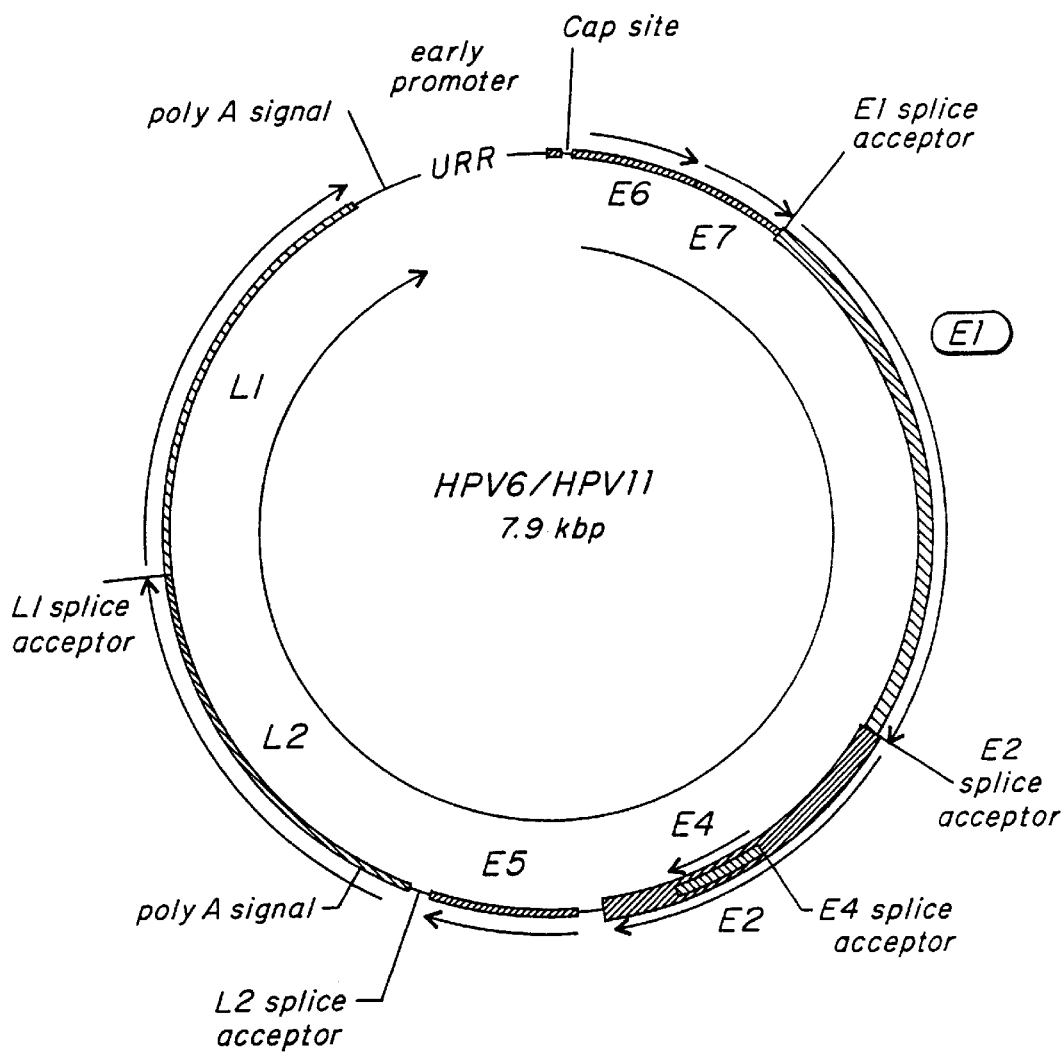
FIG. 1 is a schematic representation of the HPV genome.

E1 is one of eight viral proteins encoded by the circular, double-stranded, 7,900 base pair DNA genome of all HPV types (see FIG. 1). The genome can be divided into three distinct functional domains: the upstream regulatory region (URR), which contains the origin of viral DNA replication and enhancers and promoters involved in transcription; the L region that encodes the structural proteins, L1 and L2; and the E region that encodes genes required for vegetative functions. The eight viral proteins shown schematically in FIG. 1 are translated from complex families of alternatively spliced mRNAs.

E1 is an ATP-hydrolyzing DNA helicase which is thought to be involved in unwinding DNA at the viral origin during replication of the HPV genome by the human host DNA replication complex (Hughes et al. (1993) *Nucleic Acids Res.* 21:5817–5823; Chow et al. (1994) *Intervirol.* 37:150–158). Thus, E1 provides a virus-specific target with a defined biochemical function, which can be measured in cells expressing this gene.

In order to design a therapeutic antisense compound against human papillomaviruses, the E1 gene of HPV types 6 (Gen Bank HPV6b accession no. M14119) and 11 (Gen Bank HPV11 accession no. X00203) has been targeted. Types 6 and 11 together are associated with over 90% of cases of non-malignant genital warts. A 46 nucleotide region (from −17 to +29 of the E1 open reading frame) centered on the initiation site for protein translation has been examined in detail. This region is conserved in a number of clinical isolates of HPV types 6 and 11. The entire open reading frame of the gene (from −17 to +1950) has also been investigated as an antisense target. This entire region shows high sequence identity between HPV type 6 and HPV type 11.

It has been discovered that specific oligonucleotides complementary to particular portions of nucleic acid encoding the translational start site of human papillomavirus E1 gene can inhibit HPV replication and expression. This discovery has been exploited to provide in the present invention synthetic oligonucleotides complementary to regions spanning or beeing nearby the translational start site of mRNA encoding the HPV E1 protein.

As used herein, a "synthetic oligonucleotide" includes chemically synthesized polymers of about five and up to about 50, preferably from about 15 to about 30 ribonucleotide and/or deoxyribonucleotide monomers connected together or linked by at least one, and preferably more than one, 5' to 3' internucleotide linkage.

For purposes of the invention, the term "oligonucleotide sequence that is complementary to nucleic acid or mRNA" is intended to mean an oligonucleotide that binds to the nucleic acid sequence under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means, including in the case of an oligonucleotide binding to RNA, causing pseudoknot formation. Binding by Watson-Crick or Hoogsteen base pairing under physiological conditions is measured as a practical matter by observing interference with the function of the nucleic acid sequence.

In a first aspect, the invention provides synthetic oligonucleotides complementary to a nucleic acid spanning the translational start site of human papillomavirus gene E1, and including at least 15 nucleofides. In preferred embodiments, the oligonucleotides of the invention are from about 15 to about 30 nucleotides in length.

In some embodiments, these oligonucleotides are modified. In one embodiment, the modifications comprise at least one internucleotide linkage selected from the group consisting of alkylphosphonate, phosphorothioate, phosphorodithioate, alkylphosphonothioate, phosphoramidate, carbamate, carbonate, phosphate triester, acetamidate, or carboxymethyl ester, including combinations of such linkages, as in a chimeric oligonucleotide. In one preferred embodiment, an oligonucleotide of the invention comprises at least one phosphorothioate internucleotide linkage. In another preferred embodiment, all internucleotide linkages in the oligonucleotide are phosphorothioate internucleotide linkages. In yet another preferred embodiment, the oligonucleotide comprises at least one methylphosphonate internucleotide linkage. In a further particular embodiment, the oligonucleotide comprises at least one n-butyl phosphoromidate linkage. In one embodiment at least one methylphosphonate or n-butyl phosphoromidate linkage is at the 3' end. More preferred, about five such linkages are at the 3'-end.

In other modifications, the oligonucleotides of the invention may also include at least one deoxyribonucleotide, at least one ribonucleotide, or a combination thereof, as in a hybrid oligonucleotide. In a particular embodiment, the oligonucleotide may consist of deoxyribonucleotides only. An oligonucleotide containing at least one 2'-O-methyl ribonucleotide is one embodiment of the invention. In particular embodiments of the invention, the oligonucleotide has five 2'-O-methyl ribonucleotides at the 3' end of the oligonucleotide, or at the 3' and the 5' ends of the oligonucleotide. Other embodiments include at least one or at least two inosine residues at any position in the oligonucleotide.

More specific, in one embodiment, the oligonucleotides of the invention have a sequence set forth in Table 1A or in the Sequence Listing as SEQ ID NO:1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 36, 37, and 38. In another embodiment the oligonucleotides of the invention have a nucleotide sequence set forth in Table 1B as SEQ ID NO: 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 125, 126, 127, 128, 129, and 130. All these oligonucleotides may be further modified as outlined in the specification.

In other aspects, the invention provides a pharmaceutical composition. The pharmaceutical composition is a physical mixture of at least one, and preferably two or more HPV-specific oligonucleotides with the same or different sequences, modifications, and/or lengths. In some embodiments, this pharmaceutical formulation also includes a physiologically or pharmaceutically acceptable carrier. Specific embodiments include a therapeutic amount of a lipid carrier.

The oligonucleotides of the present invention or suitable for use as a therapeutically active compounds, especially for use in the control or prevention of human papillomavirus infection.

In this aspect of the invention, a therapeutic amount of a pharmaceutical composition containing HPV-specific synthetic oligonucleotides is administered to a cell to inhibiting human papillomavirus replication. In a similar aspect, the oligonudeotides of the present invention can be used for treating human papillomavirus infection comprising the step of administering to an infected animal or cell a therapeutic amount of a pharmaceutical composition containing at least one HPV-specific oligonucleotide, and in some embodiments, at least two HPV-specific oligonucleotides. In some preferred embodiments, the method includes administering at least one oligonucleotide, or at least two oligonucleotides, having a sequence set forth in Table 1A or in the Sequence Listing as SEQ ID NOS:1–32, 36–38, or as set forth in Table 1B as SEQ ID NOS: 41–122, 125–130, including modifications thereof.

In all methods involving the administration of oligonudeotide(s) of the invention, at least one, and preferably two or more identical or different oligonucleotides may be administered simultaneously or sequentially as a single treatment episode in the form of separate pharmaceutical compositions.

In another aspect, the invention provides a method of detecting the presence of HPV in a sample, such as a solution or biological sample. In this method, the sample is contacted with a synthetic oligonucleotide of the invention or with an oligonucleotide having the complementary sequence thereof. Hybridization of the oligonudeotide to the HPV nucleic acid is then detected if the HPV is present in the sample.

Another aspect of the invention are kits for detecting HPV in a sample. Such kits include at least one synthetic oligonucleotide of the invention or an oligonucleotide having the complementary sequence thereof, and means for detecting the oligonucleotide hybridized with the nucleic acid. In a kit having more than one oligonucleotide of the invention, these oligonucleotides may have the same or different nucleotide sequences, length, and/or modification(s).

Synthetic oligonucleotides of the invention specific for E1 nucleic acid, especially mRNA, are composed of deoxyribonucleotides, ribonucleotides, 2'-O-methyl-ribonucleotides, or any combination thereof, with the 5' end of one nucleotide and the 3' end of another nucleotide being covalently linked. These oligonucleotides are at least 6 nucleotides in length, but are preferably 12 to 50 nucleotides long, with 20 to 30mers being the most common.

These oligonucleotides can be prepared by art recognized methods. For example, nucleotides can be covalently linked using art-recognized techniques such as phosphoramidite, H-phosphonate chemistry, or methylphosphoramidite chemistry (see, e.g., Goodchild (1990) *Bioconjugate Chem*. :165–187; Uhlmann et al. (1990) *Chem. Rev.* 90:543–584; Caruthers et al. (1987) *Meth. Enzymol.* 154:287–313; U.S. Pat. No. 5,149,798) which can be carried out manually or by an automated synthesizer and then processed (reviewed in Agrawal et al. (1992) *Trends Biotechnol.* 10:152–158).

The oligonucleotides of the invention may also be modified in a number of ways without compromising their ability to hybridize to HPV nucleic acid. For example, the oligonucleotides may contain other than phosphodiester internucleotide linkages between the 5' end of one nucleotide and the 3' end of another nucleotide in which the 5' nucleotide phosphate has been replaced with any number of chemical groups, such as a phosphorothioate. Oligonucleotides with phosphorothioate linkages can be prepared using methods well known in the field such as phosphoramidite (see, e.g., Agrawal et al. (1988) *Proc. Nati. Acad. Sci.* (USA) 85:7079–7083) or H-phosphonate (see, e.g., Froehler (1986) *Tetrahedron Lett*. 27:5575–5578) chemistry. The synthetic methods described in Bergot et al. (*J. Chromatog*. (1992) 559:35–42) can also be used. Examples of other chemical groups which may form an internucleotide linkage include alkylphosphonates, phosphorodithioates, alkylphosphonothioates, phosphoramidates, carbamates, acetamidates, carboxymethyl esters, carbonates, and phosphate triesters.

As an example, for a combination of internucleotide linkages, U.S. Pat. No. 5,149,797 describes traditional chimeric oligonucleotides having a phosphorothioate core region interposed between methylphosphonate or phosphoramidate flanking regions. Other chimerics are "inverted" chimeric oligonucleotides comprising one or more nonionic oligonucleotide regions (e.g. alkylphosphonate and/or phosphoramidate and/or phosphotriester internucleoside linkage) flanked by one or more regions of oligonucleotide phosphorothioates. Chimerics and inverted chimerics may be synthesized as discussed in the Examples for methyl phosphonate containing oligonucleotides. These "chimerics" and "inverted chimeric" oligonucleotides are a preferred embodiment for the modification of the oligonucleotides of the present invention.

Various oligonucleotides with modified internucleotide linkages can be prepared according to known methods (see, e.g., Goodchild (1990) *Bioconjugate Chem.* 2:165–187; Agrawal et al. (1988) *Proc. Natl. Acad. Sci.* (USA) 85:7079–7083; Uhlmann et al. (1990) *Chem. Rev.* 90:534–583; and Agrawal et al. (1992) *Trends Biotechnol.* 10:152–158).

Oligonucleotides which are self-stabilized are also considered to be modified oligonucleotides useful in the methods of the invention (Tang et al. (1993) *Nucleic Acids Res.* 20:2729–2735). These oligonucleotides comprise two regions: a target hybridizing region; and a self-complementary region having an oligonucleotide sequence complementary to a nucleic acid sequence that is within the self-stabilized oligonucleotide. These oligos form looped structures which are believed to stabilize the 3' end against exonuclease attack while still allowing hybridization to the target.

On the other hand, examples of modifications to sugars include modifications to the 2' position of the ribose moiety which include but are not limited to 2'-O-substituted with an —O—lower alkyl group containing 1–6 saturated or unsaturated carbon atoms, or with an —O—aryl, or allyl group having 2–6 carbon atoms wherein such —O—alkyl, aryl or allyl group may be unsubstituted or may be substituted (e.g., with halogen, hydroxy, trifluoromethyl, cyano, nitro, acyl, acyloxy, alkoxy, carboxy, carbalkoxyl, or amino groups), or wherein the 2-O— group is substituted by an amino, or halogen group. None of these substitutions are intended to exclude the native 2' -hydroxyl group in case of ribose or 2'-H- in the case of deoxyribose. PCT Publication No. WP 94/02498 discloses traditional hybrid oligonucleotides having regions of 2'-O-substituted ribonucleotides flanking a DNA core region. Another form of a hybrid is an "inverted" hybrid oligonucleotide which includes an oligonucleotide comprising a 2'O-substituted (or 2' OH unsubstituted) RNA region which is interposed between two oligodeoxyribonucleotides regions, a structure that is inverted relative to the "traditional" hybrid oligonucleotides. Hybrid and inverted hybrid oligonucleotides may be synthesized as described in the Examples for oligonucleotides containing 2'-O-methyl RNA. The hybrid and inverted hybrid oligonucleotides of the invention are particularly preferred due to the enhanced stability and activity over time in the presence of serum. In another embodiment the hybrid or inverted hybrid oligonucleotide may comprise at least one n-butyl phosphoramidate or methylphosphonate linkage.

Preferably, the ribonucleotide is a 2'-O-methyl ribonucleotide. In another embodiment, the oligonucleotide comprises at least one, preferably one to five 2'-O-methyl ribonucleotides at the 3' end of the oligonucleotide. Moreover, the oligonucleotide may further comprise at least one, preferably one to five 2'-O-methyl ribonucleotides at the 5'-end.

Other oligonucleotide structures of the invention include the so-called dumbell and nicked dumbell structures (Table 1B). Ashly and Kushlan (*Biochem*. (1991) 30:2927–2933) describe the synthesis of oligonucleotide dumbells including nicked dumbells. A dumbbell is a double-helical stem closed off by two hairpin loops. The antisense activity of nicked dumbbells (dumbbell molecules with free ends) is discussed by Yamakawa et al. (*Nucleosides and Nucleotides* (1996) 15:519–529). These structures are believed to have beneficial properties similar to those of the self-stabilized oligos described above.

Other modifications include those which are internal or are at the end(s) of the oligonucleotide molecule and include additions to the molecule at the internucleoside phosphate linkages, such as cholesteryl, cholersterol, or diamine compounds with varying numbers of carbon residues between the two amino groups, and terminal ribose, deoxyribose and phosphate modifications which cleave, or crosslink to the opposite chains or to associated enzymes or other proteins which bind to the viral genome. Additional linkers including non-nucleoside linkers include, but are not limited to, polyethylene glycol of varying lengths, e.g., triethylene glycol, monoethylene glycol, hexaethylene glycol, (Ma et al. (1993) *Nucleic Acids Res*. 21:2585–2589; Benseler et al. (1993) *J. Am. Chem. Soc*. 115:8483–8484), hexylamine, and stilbene (Letsinger et al, (1995) *J. Am. Chem. Soc*. 117:7323–7328) or any other commercially available linker including abasic linkers or commercially available asymetric and symetric linkers (CloneTech, Palo Alto, Calif.) (e.g., Glen Research Product Catalog, Sterling, Va.).

Other examples of modified oligonucleotides include those with a modified base and/or sugar such as arabinose instead of ribose, or a 3', 5'-substituted oligonucleotide having a sugar which, at one or both its 3' and 5' positions is attached to a chemical group other than a hydroxyl or phosphate group (at its 3' or 5' position).

Additionally oligonucleotides capped with ribose at the 3' end of the oligonucleotide may be subjected to $NaIO_4$ oxidation/reductive amination. Examples of such species may be found in Table 1B. Amination may include but is not limited to the following moieties, spermine, spermidine, Tris(2-aminoethyl) amine (TAEA), DOPE, long chain alkyl amines, crownethers, coenzyme A, AND, sugars, peptides, dendrimers.

In a further embodiment, at least one cytosine bases may be modified by methylation as is known in the art, e.g. 5-methylated deoxycytosine (5-Me-dC) (see Table 1B). Such methylation may be desirable, for example, to reduce immune stimulation by the oligonucleotide if necessary.

Other modified oligonucleotides are capped with a nudease resistance-conferring bulky substituent at their 3' and/or 5' end(s), or have a substitution in one or both nonbridging oxygens per nucleotide. Such modifications can be at some or all of the internucleoside linkages, as well as at either or both ends of the oligonucleotide and/or in the interior of the molecule (reviewed in Agrawal et al. (1992) *Trends Biotechnol*. 10:152–158). Some non-limited examples of capped species include 3' O-methyl, 5' O-methyl, 2' O-methyl, and any combination thereof, as shown in Table 1B.

In a preferred embodiment, the oligonucleotide has a complementary nucleotide sequence selected from the group of (SEQ ID NOS:1 (HPV1), 11 (HPV19), 14 (HPV22), 15 (HPV23), 18 (HPV30), 19 (HPV31), 20 (HPV32), 21 (HPV33) and 26 (HPV39) as shown in Table 1A, including modifications thereof.

In another embodiment, the oligonucleotide has a nucleotide sequence selected from the group of (SEQ ID NOS: 54 (HPV56), 118 (HPV53), 119 (HPV52) and 121 (HPV 50)) as shown in Table 1B, including modifications thereof.

In a specific embodiment, these oligonucleotides of the two embodiments mentioned before consist of deoxyribonucleotides and have phosphorthioate internucleotide linkages.

In another specific embodiment, the oligonucleotide is selected from the group of sequences having SEQ ID NOS: 1, 41–122 and 125–130 as given in Table 1B and wherein the oligonucleotide has the internucleotide linkage composition and further modifications as set forth in Table 1B.

Most preferred the oligonucleotide has a nucleotide sequence and further modifications as specified for an oligonucleotide selected from the group consisting of SEQ ID NOS: 88 (HPV1 8-4-8 IH 2'-OMe PO), 88 (HPV1 8-4-8 IH 2'-OMe PS), 89 (7-6-7 IH 2'-OMe PO), 89 (7-6-7 IH 2'-OMe PS), 90 (HPV1 9-6-5 IH 2'-OMe PO), 90 (HPV1 9-6-5 IH 2' OMe PS), 91 (5-6-9 IH 2'-OMe PO), 91 (5-6-9 IH 2'-OMe PS), 92 (10-6-4 IH 2'-OMe PO), 92 (10-6-4 IH 2'-OMe PS), 93 (HPV1 6-8-6 IH 2'-OMe PO) and 93(HPV1 6-8-6 IH 2'-OMe PS)., from SEQ ID NOS: 41(SS1), 42 (SS2), 43 (SS3), 44 (SS4), 49 (SS9) and 51(SS11), from SEQ ID NOS: 54 (HPV56 CAP), 57 (SS16), 59 (SS18), 65 (SS26), 67 (SS28) and 104 (HPV56. 0×5 Hybrid), and from SEQ ID NOS: 1 (HPV1 5-Me-dC), 24 (HPV36 5-Me-dC) and 112 (HPV43 5-Me-dC).

20 mer phosphorothioate oligonucleotides complementary to the E1 gene of HPV strain 6a and 6b (in vitro transcribed RNA=2328 bases) were tested with a ribonuclease H (RNase H) assay using 100 nM synthetic oligonucleotide and in vitro transcribed RNA. The RNase H assay identified regions of the target RNA that were accessible to the antisense oligonucleotide; cleavage indicated that the oligonucleotide had hybridized with the target RNA to an extent that the target was digested by RNase H. The results of RNase H-mediated cleavage are shown in Table 1A. Position +1 of the E1 target site is the first base of the translation start site.

TABLE 1A

| Oligo | Sequence (5'- >3') | E1 target site | % RNase H cleavage | SEQ ID NO: |
|---|---|---|---|---|
| HPV1 | GTACCTGAATCGTCCGCCAT | +1→+20 | 60 | 1 |
| HPV2 | CATCGTTGTTAGGTCTTCGG | −17→+3 | 33 | 2 |
| HPV3 | TCGTCCGCCATCGTTGTTAG | −9→+11 | 62 | 3 |
| HPV4 | CCGCCATCGTTGTTAGGTCT | −13→+7 | 58 | 4 |
| HPV5 | TGAATCGTCCGCCATCGTTG | −5→+15 | 57 | 5 |
| HPV6 | CATTTTCTGTACCTGAATCG | +9→+28 | 31 | 6 |
| HPV11 | GTACCTGAATCGTCCGCCAT CGTTGTTA | −8→+20 | 80% of HPV1 | 7 |
| HPV15 | GTACCTGAATCGTCCGCCAT CGTTG | −5→+20 | 96% of HPV1 | 8 |
| HPV17 | TTTTCTGTACCTGAATCGTC | +7→+26 | 28 | 9 |
| HPV18 | CCCCTCATTTTCTGTACCTG | +14→+33 | 8 | 10 |
| HPV19 | ACCCAGACCCCTCATTTTCT | +21→+40 | 22 | 11 |
| HPV20 | GGGTGTCCGCCTCCTGCCTG | +203→+222 | 34 | 12 |
| HPV21 | CGTTTTAGGTCCTGCACAGT | +231→+250 | 8 | 13 |
| HPV22 | GCCTCGGCTATAGTGTTTAT | +282→+301 | 19 | 14 |
| HPV23 | CGTCGCTTTACCTTTTTTGG | +373→+392 | 57 | 15 |
| HPV26 | CCAGACCCCTCATTTTCTGT | +19→+38 | 35 | 16 |
| HPV27 | ATAAACCATCCTGTACACCC | +37→+56 | 18 | 17 |
| HPV30 | CCTGAATCGTCCGCCAT | +1→+17 | | 18 |
| HPV31 | GTACCTGAATCGTCCGCCA | +2→+20 | | 19 |
| HPV32 | TACCTGAATCGTCCGCCAT | +1→+19 | | 20 |
| HPV33 | ACCTGAATCGTCCGCCAT | +1→+18 | | 21 |

TABLE 1A-continued

| Oligo | Sequence (5'- >3') | E1 target site | % RNase H cleavage | SEQ ID NO: |
|---|---|---|---|---|
| HPV34 | CTGAATCGTCCGCCAT | +1→+16 | | 22 |
| HPV35 | GTACCTGAATCGTCC | +6→+20 | | 23 |
| HPV36 | GTACCTGAATCGTCCG | +5→+20 | | 24 |
| HPV37 | GTACCTGAATCGTCCGC | +4→+20 | | 25 |
| HPV38 | GTACCTGAATCGTCCGCC | +3→+20 | | 26 |
| HPV39 | TGAATCGTCCGCCAT | +1→+15 | | 27 |
| HPV40 | GTACCTGAATCGTCCGCCAT CGTTGTTAGG | −10→+20 | | 28 |
| HPV24[a] | tctttttttttTTTTCTGTAC CTGAATCGTC | +7→+26 | | 29 |
| HPV28[a] | ACCCAGACCCCTCATTTTCT tttttcttt | +21→+40 | | 30 |
| HPV7[b] | GTACCTaAATCGTCCGCCAT | +1→+20 | 100% of HPV1 | 31 |
| HPV8[b] | GTACCTaAATCaTCCGCCAT | +1→+20 | 52% of HPV1 | 32 |
| HPV9[b] | GTACCTaAATCaTCCaCCAT | +1→+20 | | 33 |
| HPV10[b] | aTACCTaAATCaTCCaCCAT | +1→+20 | | 34 |
| HPV29[b] | GTgCCaGAgTCGTCCGCCAT | +1→+20 | | 35 |
| HPV12[b] | GTACCTiAATCaTCCGCCAT | +1→+20 | 61% of HPVI | 36 |
| HPV13[b] | GTACCTaAATCITCCGCCAT | +1→+20 | 74% of HPV1 | 37 |
| HPV14[b] | GTACCTiAATCiTCCGCCAT | +1→+20 | 81% of HPV1 | 38 |

[a] potential triplex forming oligonucleotide
[b] lower case letter represents a mismatched base
italicized letters represent triplex-forming bases
Internucleotide linkage is PS unless otherwise mentioned These results suggest that the region close to the translation start site (AUG) is accessible to antisense oligonucleotides and susceptible to cleavage with RNase H. The data further define a very active region for hybridization and cleavage from −13 to +20. The best of these oligonucleotides were HPV1 (+1 to +20) (SEQ ID NO:1), HPV3 (−9 to +11) (SEQ ID NO:3), HPV4 (−13 to +7) (SEQ ID NO:4) and HPV5 (−5 to +15) (SEQ ID NO:5).

In addition, four regions in the downstream coding region that appear to be accessible to hybridization by antisense oligonucleotides were identified using the randomer RNase H assay. The oligonucleotides prepared that bind to these regions are HPV20 (+203 to +222) (SEQ ID NO:12), HPV21 (+231 to +250) (SEQ ID NO: 13), HPV22 (+282 to +301) (SEQ ID NO:14), and HPV23 (+373 to +392) (SEQ ID NO:15). The results are shown in Table 1A. The data suggest that the region at +373 is the site most susceptible to RNase H cleavage in the presence of its complementary DNA phosphorothioate sequence.

The oligonucleotides identified outside the E1 luciferase fusion target sequences can be assayed by examining expression of the full length E1 gene product (see Example 6 below).

These and other antisense oligonucleotides targeted to the translation start site were tested in mammalian cells using firefly luciferase reporter gene assays. The 46 nucleotide region of the HPV E1 gene from −17 to +29 nucleotides relative to the translation start site was cloned 5' to, and in frame with, the entire open reading frame of the firefly luciferase gene in the plasmid pGLori, to produce the plasmid pE1Luc6. Transcription of this E1-luciferase gene fusion was placed under the control of the cytomegalovirus early gene promoter. Expression of the E1-luciferase fusion in mammalian cells was quantified in a luminometer by addition of luciferin substrate and ATP cofactor to cell lysates. The reduction in luciferase levels in cells treated with antisense oligonucleotides compared to luciferase levels in cells treated with a negative control random oligonucleotide is a measure of the sequence specific activity of the antisense oligonucleotides.

In all cellular antisense assays, a random sequence 20 mer phosphorothioate oligonucleotide was used as a negative control compound. In addition a 20 mer phosphorothioate antisense oligonucleotide targeting the first 20 nucleotides of the coding region of the firefly luciferase gene was used as a positive control (Luc +1–+20) (SEQ ID NO:39). This target is retained in both the E1 fusion and control luciferase constructs.

Figure 2:
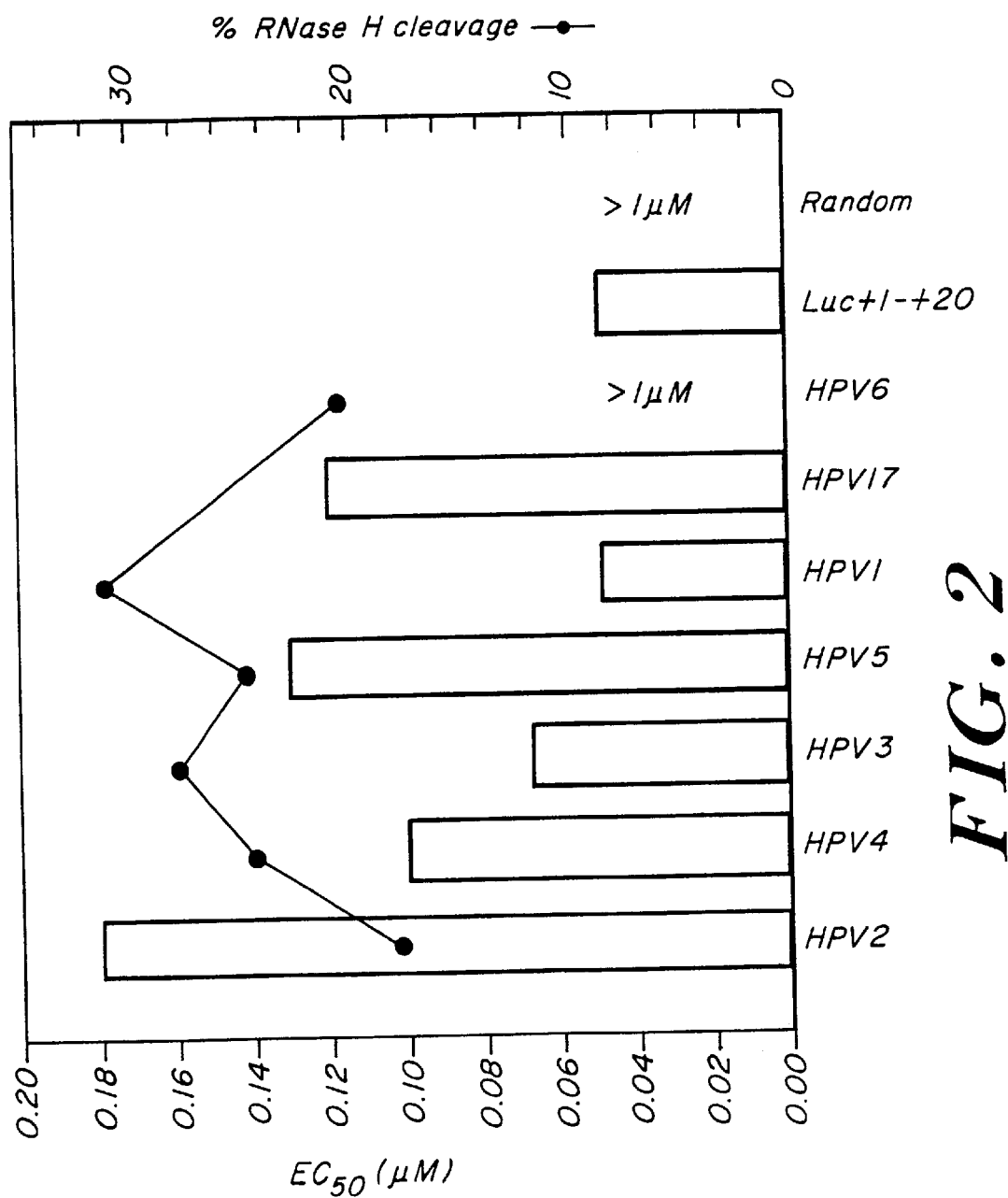
FIG. 2 is a graphic representation of the antisense activity of 20 mer PS oligonucleotides in stably transfected cells and corresponding RNase H activity.

Chinese Hamster Ovary (CHO-K1) cells were stably transfected with the pE1Luc6 construct. The percentage of luciiferase expression measured relative to the control effective concentration ($EC_{50}$) was then measured of the oligonucleotide that yields inhibition equal to 50% of control (i.e:, cells treated with lipid only). Phosphorothioate (PS) 20 mer oligonucleotides 1, 3, 4, 5, and 17 all exhibited sequence specific antisense activity against the E1Luc6 target, as did the positive control Luc +1–+20 PS antisense oligonucleotide targeted against the first 20 nucleotides of the luciferase gene coding region. Two E1-specific 20 mer oligonucleofides, 2 and 6, and the random PS 20 mer negative control oligonucleotide showed little or no activity (FIG. 2). There was good correlation between the in vitro RNase H cleavage of the target RNA and the sequence specific antisense activity in the stably transfected cells (FIG. 2). None of the oligonucleotides, with the exception of the positive control Luc +1–+20 oligonucleotide, exhibited sequence specific antisense activity in CHO-K1 cells stably transfected with the parent pGLori construct that carries the luciferase gene alone.

Other oligonucleotides listed in Table 1B below also exhibited activity.

TABLE 1B

| Oligo | SEQ ID NO: | Sequence (5'-3') | Loop Size | $EC_{50}$ (nM) | Description |
|---|---|---|---|---|---|
| HPV1 CAP | 1 | GTACCTGAATCGTCCGCCAT-NH$_2$ | | 44 | 20mer PS/3' 3-amino-2-propanol CAP |
| SS1 | 41 | GTACCTGAATCGTCCGCCAT-L-atggc | L | 27 | 25mer + PEG loop |
| SS2 | 42 | GTACCTGAATCGTCCGCCAT-tttt-atggc | 4 | 22 | 29mer/4 base loop/5 base stem |
| SS3 | 43 | GTACCTGAATCGTCCGCCAT-ttt-atggc | 3 | 24 | 28mer/3 base loop/5 base stem |
| SS4 | 44 | GTACCTGAATCGTCCGCCAT-tt-atggc | 2 | 25 | 27mer/2 base loop/5 base stem |
| SS5 | 45 | GTACCTGAATCGTCCGCCAT-t-atggc | 1 | 61 | 26mer/1 base loop/5 base stem |
| SS6 | 46 | GTACCTGAATCGTCCGCCAtggc | 0 | 67 | 25mer/0 base loop/5 base stem |
| SS7 | 47 | GTACCTGAATCGTCCGCCAtggc | 1 | 46 | 24mer/1 base loop/4 base stem |
| SS8 | 48 | GTACCTGAATCGTCCgccatggacg | 4 | 45 | 25mer/5 base loop/5 base stem |
| SS9 | 49 | GTACCTGAATCGTCCgccatggac | 5 | 34 | 24mer/5 base loop/4 base stem |
| SS10 | 50 | GTACCTGAATCGTCCgccatgga | 5 | 48 | 23mer/5 base loop/3 base stem |
| SS11 | 51 | GTACCTGAATCGTCCGCCATtca | 8 | 30 | 23mer/8 base loop/5 base stem |
| SS12 | 52 | GTACCTGAATCGTCCGCCATggtac | 15 | 61 | 25mer/15 base loop/5 base stem |
| SS13 | 53 | gatGTACCTGAATCGTCCGCCATc | 15 | 88 | 25mer/15 base loop/5 base stem |
| HPV56 | 54 | CTGAATCGTCCGCCATC | | 81 | E1 −1 > +16 |
| HPV56 CAP | 54 | CTGAATCGTCCGCCATC-NH2 | | 48 | 17mer PS/3' 3-amino-2-propanol CAP |
| SS14 | 55 | CTGAATCGTCCGCCATC-L-gatgg | L | 55 | 22mer + PEG loop |
| SS15 | 56 | CTGAATCGTCCGCCATC-tttt-gatgg | 4 | 94 | 26mer/4 base loop/5 base stem |
| SS16 | 57 | CTGAATCGTCCGccatCggac | 4 | 35 | 21mer/4 base loop/5 base stem |
| SS17 | 58 | CTGAATCGTCCGccatCgga | 4 | 60 | 20mer/4 base loop/4 base stem |
| SS18 | 59 | CTGAATCGTCCGccatCgg | 4 | 43 | 19mer/4 base loop/3 base stem |
| SS19 | 60 | CTGAATCGTCCGCCATCgatt | 8 | 53 | 21mer/8 base loop/5 base stem |
| SS20 | 61 | cCTGAATCGTCCGCCATCagg | 11 | 47 | 21mer/11 base loop/5 base stem |
| SS21 | 62 | CTGAATCGTCCGCCATCag | 11 | 73 | 19mer/11 base loop/4 base stem |
| SS22 | 63 | CTGAATCGTCCGCCATC-uggcc-uuuu-ggcca | 4 | 65 | 2'OmePS 5 base stem/4 base loop |
| SS23 | 64 | CTGAATCGTCCGCCATC-uggcc-L-ggcca | L | 93 | 2'OMePS 5 base stem/PEG loop |

TABLE 1B-continued

| Oligo | SEQ ID NO: | Sequence (5'-3') | Loop Size | EC$_{50}$ (nM) | Description |
|---|---|---|---|---|---|
| SS24 | 63 | CTGAATCGTCCGCCATC-uggcc-uuuu-ggcca | 4 | 66 | 2'OMePO 5 base stem/4 base loop |
| SS25 | 64 | CTGAATCGTCCGCCATC-uggcc-L-ggcca | L | 102 | 2'PMePO 5 base stem/PEG loop |
| SS26 | 65 | CTGAATCGTCCGCCATC-tggcc-tttt-ggcca | 4 | 34 | 31mer/4base loop/5 base stem 3' |
| SS27 | 66 | CTGAATCGTCCGCCATC-tggcc-L-ggcca | L | 51 | 27mer/PEG loop/5 base stem 3' |
| SS28 | 67 | ggccatttttggcc-CTGAATCGTCCGCCATC | 4 | 33 | 31mer/4base loop/5 base stem 5' |
| SS29 | 68 | ggcca-L-tggcc-CTGAATCGTCCGCCATC | L | 46 | 27mer/PEG loop/5 base stem 5' |
| SS30 | 69 | tggcc-CTGAATCGTCCGCCATC-tttt-ggcca | 21 | 48 | 31mer/21base 3'-loop/5 base stem |
| SS31 | 70 | tggcc-CTGAATCGTCCGCCATC-L-ggcca | 17/L | 70 | 31mer/17base 3'-loop + PEG/5base stem |
| SS32 | 71 | ggccatttt-CTGAATCGTCCGCCATC-tggcc | 21 | 40 | 31mer/21base 5'-loop/5 base stem |
| SS33 | 72 | ggcca-L-CTGAATCGTCCGCCATC-tggcc | 17/L | 97 | 31mer/17base 5'-loop+PEG/5base stem |
| SS34 | 73 | ggcca-L-CTGAATCGTCCGCCATC-L-tggcc | 17/2L | 86 | 31mer/17base 5'-loop+PEG/5base stem |
| HPV60 (-4 TO +16) | 74 | CTGAATCGTCCGCCATCGTT | — | | |
| SS35 | 75 | CTGAATCGTCCGCCATCGTT-tggcg | 5 | | 26mer/5 base loop/5 base stem |
| HPV59 (-5 to +16) | 76 | CTGAATCGTCCGCCATCGTTG | — | | |
| SS40 | 77 | CTGAATCGTCCGCCATCGTTG-atgg | 3 | | 25mer/3 base loop/5 base stem |
| SS41 | 78 | CTGAATCGTCCGCCATCGTTG-atggc | 3 | | 26mer/3 base loop/6 base stem |
| SS42 | 79 | CTGAATCGTCCGCCATCGTTG-atggcg | 3 | | 27mer/3 base loop/7 base stem |
| SS36 | 80 | GTACCTGAATCGTCCGCCAT-t-L(OH)-t-atgga | 2+L | | L-asymmetric amidite C$_3$ linker |
| SS37 | 80 | GTACCTGAATCGTCCGCCAT-t-L(Chol)-t-atggc | 2+L | | L-asym.amidite;Chol=cholesterol |
| SS38 | 80 | GTACCTGAATCGTCCGCCAT-t-L(C6NH$_2$)-t-atggc | 2+L | | L = asym.amidite;C6NH$_2$=5'-amino Modifier 6 |
| SS39 | 80 | GTACCTGAATCGTCCGCCAT-t-L(PEG)-t-atggc | 2+L | | L = asym.amidite;PEG=(OCH$_2$CH$_2$)$_6$O |
| SS3 0x8 2'-OMe | 81 | GTACCTGAATCGTCCGCCAT-uuu-auggc | 3 | | 28mer/3 base loop/5 base stem/0x8 hybrid |
| SS3I 15x5 Inv. 2'-OMe | 82 | GTACCTGAATCGTCCGCCAU-uuu-atggc | 3 | | 28mer/3 base loop/5 base stem/inv.hyb |
| SS3 0x13 2'-OMe | 83 | GTACCTGAATCGTCCGCGAU-uuu-auggc | 3 | | 28mer/3 base loop/5 base stem/3'hybrid |
| SS43 | 80 | GTACCTGAATCGTCCGCCAT-t-L(OH)-t-atggc-Chol | 2+L | | L = asymmetric amidite/Chol=cholesterol 3'-cholesterol |
| SS44 | 80 | Chol-GTACCTGAATCGTCCGCCAT-t-L(OH)-t-atggc | 2+L | | L = asymmetric amidite/Chol=cholesterol 5'-cholesterol |
| SS45 | 80 | GTACCTGAATCGTCCGCCAT-t-L(Chol)-t-atgga-chol | 2+L | | L = asym.amidite;Chol=cholesterol 3'/loop bis(cholesterol) |
| SS46 | 80 | chol-GTACCTGAATCGTCCGCCAT-t-L(Chol)-t-atggc | 2+L | | L = asym.amidite;Chol=cholesterol 5'/loop bis(cholesterol) |
| SS47 | 80 | Chol-GTACCTGAATCGTCCGCCAT-t-L(OH)-t-atggc-Chol | 2+L | | L = asym.amidite;Chol=cholesterol 3'/5' bis(cholesterol) |
| SS48 | 80 | Chol-GTACCTGAATCGTCCGCCAT-t-L(Chol)-t-atggc-Chol | 2+L | | L = asym.amidite;Chol=cholesterol 3'/5'/loop Tris(cholesterol) |
| SS49 | 84 | ATTCAGgtacCTGAAT CGTCCGccatCGGACG | 4/4 | | 32mer Symmetric Nicked Dumbell |

TABLE 1B-continued

| Oligo | SEQ ID NO: | Sequence (5'-3') | Loop Size | EC₅₀ (nM) | Description |
|---|---|---|---|---|---|
| SS50 | 85 | ATTCAG<sub>TAC</sub>CTGAAT CGTCC<sub>GCCAT</sub>GGACG | 3/5 | | 30mer Symmetric Nicked Dumbell |
| SS51 | 86 | GATTCAG<sub>TAC</sub>CTGAATC GTCC<sub>GCCAT</sub>GGAC | 3/5 | | 30mer Asymmetric Nicked Dumbell |
| SS52 | 87 | GATTCAG<sub>GTAC</sub>CTGAATC GTCCG<sub>CCAT</sub>CGGAC | 4/4 | | 32mer Asymmetric Nicked Dumbell |
| HPV1 8-4-8 IH 2'-OMe PO | 88 | GTACCTGA-<u>AUCG</u>-TCCGCCAT | | 53 | DNA PS-2'-OMe PO-DNA PS Hybrid |
| HPV1 8-4-8 IH 2'-OMe PS | 88 | GTACCTGA-<u>AUCG</u>-TCCGCCAT | | 24 | DNA PS-2'-OMe PS-DNA PS Hybrid |
| HPV1 7-6-7 IH 2'-OMe PO | 89 | GTACCTG-<u>AAUCGU</u>-CCGCCAT | | 52 | DNA PS-2'-OMe PO-DNA PS Hybrid |
| HPV1 7-6-7 IH 2'-OMe PS | 89 | GTACCTG-<u>AAUCGU</u>-CCGCCAT | | 24 | DNA PS-2'-OMe PS-DNA PS Hybrid |
| HPV1 9-6-5 IH 2'-OMe PO | 90 | GTACCTGAA-<u>UCGUCC</u>-GCCAT | | 40 | DNA PS-2'-OMe PO-DNA PS Hybrid |
| HPV1 9-6-5 IH 2'-OMe PS | 90 | GTACCTGAA-<u>UCGUCC</u>-GCCAT | | 21 | DNA PS-2'-OMe PS-DNA PS Hybrid |
| HPV1 5-6-9 IH 2'-OMe PO | 91 | GTACC-<u>UGAAUC</u>-GTCCGCCAT | | 62 | DNA PS-2'-OMe PO-DNA PS Hybrid |
| HPV1 5-6-9 IH 2'-OMe PS | 91 | GTACC-<u>UGAAUC</u>-GTCCGCCAT | | 27 | DNA PS-2'-OMe PS-DNA PS Hybrid |
| HPV1 10-6-4 IH 2'-OMe PO | 92 | GTACCTGAAT-<u>CGUCCG</u>-CCAT | | 63 | DNA PS-2'-OMe PO-DNA PS Hybrid |
| HPV1 10-6-4 IH 2'-OMe PS | 92 | GTACCTGAAT-<u>CGUCCG</u>-CCAT | | 21 | DNA PS-2'-OMe PS-DNA PS Hybrid |
| HPV1 6-8-6 IH 2'-OMe PO | 93 | GTACCT-<u>GAAUCGUC</u>-CGCCAT | | 66 | DNA PS-2'-OMe PO-DNA PS Hybrid |
| HPV1 6-8-6 IH 2'-OMe PS | 93 | GTACCT-<u>GAAUCGUC</u>-CGCCAT | | 30 | DNA PS-2'-OMe PS-DNA PS Hybrid |
| HPV1 8-4-8 IH MP | 1 | GTACCTGA-ATCG-TCCGCCAT | | | DNA PS-MP-DNA PS Chimera |
| HPV1 7-6-7 IH MP | 1 | GTACCTG-AATCGT-CCGCCAT | | | DNA PS-MP-DNA PS Chimera |
| HPV1 9-6-5 IH MP | 1 | GTACCTGAA-TCGTCC-GCCAT | | | DNA PS-MP-DNA PS Chimera |
| HPV1 5-6-9 IH MP | 1 | GTACC-TGAATC-GTCCGCCAT | | | DNA PS-MP-DNA PS Chimera |
| HPV1 10-6-4 IH MP | 1 | GTACCTGAAT-CGTCCG-CCAT | | | DNA PS-MP-DNA PS Chimera |
| HPV1 6-8-6 IH MP | 1 | GTACCT-GAATCGTC-CGCCAT | | | DNA PS-MP-DNA PS Chimera |
| HPV58 | 94 | GTACCTGAATCITCCICCAT | | | CpG --> CpI |
| HPV1 5X5 HYBRID | 95 | <u>GUACC</u>-TGAATCGTCC-<u>GCCAU</u> | | 56 | 5' and 3' 2'-OMe Caps |
| HPV1 0X5 HYBRID | 96 | GTACCTGAATCGTCC-<u>GCCAU</u> | | 53 | 3' 2'-OMe Caps |
| HPV1 4X4 HYBRID | 97 | <u>GUAC</u>-CTGAATCGTCCG-<u>CCAU</u> | | 35 | 5' and 3' 2'-OMe Caps |
| HPV1 2x4 HYBRID | 98 | <u>GU</u>-ACCTGAATCGTCCG-<u>CCAU</u> | | 40 | 5' and 3' 2'-OMe Caps |
| HPV1 0X4 HYBRID | 99 | GTACCTGAATCGTCCG-<u>CCAU</u> | | 58 | 3' 2'-OMe Caps |
| HPV1 0X3 HYBRID | 100 | GTACCTGAATCGTCCGC-<u>CAU</u> | | 75 | 3' 2'-OMe Caps |
| HPV1 0X2 HYBRID | 101 | GTACCTGAATCGTCCGCC-<u>AU</u> | | 67 | 3' 2'-OMe Caps |
| HPV1 0X1 HYBRID | 102 | GTACCTGAATCGTCCGCCA-<u>U</u> | | 28 | 3' 2'-OMe Caps |
| HPV56 5X5 HYBRID | 103 | <u>CUGAA</u>-TCGTCCG-<u>CCAUC</u> | | 113 | 5' and 3' 2'-OMe Caps |
| HPV56 0X5 HYBRID | 104 | CTGAATCGTCCG-<u>CCAUC</u> | | 36 | 3' 2'-OMe Caps |
| HPV56 4X4 HYBRID | 105 | <u>CUGA</u>-ATCGTCCGC-<u>CAUC</u> | | 78 | 5' and 3' 2'-OMe Caps |
| HPV56 0X4 HYBRID | 106 | CTGAATCGTCCGC-<u>CAUC</u> | | 81 | 3' 2'-OMe Caps |
| HPV56 3X3 HYBRID | 107 | <u>CUG</u>-AATCGTCCGCC-<u>AUC</u> | | 89 | 5' and 3' 2'-OMe Caps |
| HPV56 0X3 HYBRID | 108 | CTGAATCGTCCGCC-<u>AUC</u> | | 164 | 3' 2'-OMe Caps |
| HPV56 2X4 HYBRID | 109 | <u>CU</u>-GAATCGTCCGC-<u>CAUC</u> | | 68 | 5' and 3' 2'-OMe Caps |
| HPV1 5-Me-dC | 1 | GTACCTGAATCGTCCGCCAT | | 29 | 5-Me-dC |

TABLE 1B-continued

| Oligo | SEQ ID NO: | Sequence (5'-3') | Loop Size | EC$_{50}$ (nM) | Description |
|---|---|---|---|---|---|
| HPV36 5-Me-dC | 24 | GTACCTGAATCGTCCG | | 18 | 5-Me-dC |
| HPV36 4X4 HYBRID | 110 | <u>GUAC</u>-CTGAATCG-<u>UCCG</u> | | 117 | 5' and 3' 2'-OMe Caps |
| HPV36 0X4 HYBRID | 111 | GTACCTGAATCG-<u>UCCG</u> | | 72 | 3' 2'-OMe Caps |
| HPV43 5-Me-dC | 112 | ATCGTCCGCCAT | | 88 | 5-Me-dC |
| HPV43 4X4 HYBRID | 113 | <u>AUCG</u>-TCCG-<u>CCAU</u> | | 283 | 5' and 3' 2'-OMe Caps |
| HPV43 0X4 HYBRID | 114 | ATCGTCCG-<u>CCAU</u> | | 150 | 3' 2'-OMe Caps |
| HPV1 C15 5-Me-dC | 1 | GTACCTGAATCGTCCGCCAT | | 35 | C at position 15=5-Me-dC |
| HPV1 C11 5-Me-dC | 1 | GTACCTGAATCGTCCGCCAT | | 31 | C at position 11=5-Me-dC |
| HPV1 C11,C15 5-Me-dC | 1 | GTACCTGAATCGTCCGCCAT | | 19 | C at position 11 and 15=5-Me-dC |
| HPV57(-1 to +16 5'-SR) | 115 | XYZ-CTGAATCGTCCGCCATC | | 32 | X=A,G,C; Y=C,G,T; Z=A,G,T Semirandom Control |
| HPV55 (+6 TO +25) | 116 | TTTCTGTACCTGAATCGTCC | | 72 | |
| HPV54 (+5 TO +24) | 117 | TTCTGTACCTGAATCGTCCG | | 136 | |
| HPV53 (+4 TO +23) | 118 | TCTGTACCTGAATCGTCCGC | | 98 | |
| HPV52 (+3 TO +22) | 119 | CTGTACCTGAATCGTCCGCC | | 51 | |
| HPV51 (+2 TO +21) | 120 | TGTACCTGAATCGTCCGCCA | | 71 | |
| HPV50 (-1 TO +19) | 121 | TACCTGAATCGTCCGCCATC | | 70 | |
| HPV49M (MP/ps) | 122 | GTACCTGAATCGTCCGCCA-TCCTT | | | 3'-methyl phosphonate cap |
| HPV49 (-4 TO +20) | 122 | GTACCTGAATCGTCCGCCATCCTT | | | HPV TYPE 11 SEQ |
| HPV48 | 123 | TACCGCCTGCTAAGTCCATG | | >1000 | Scrambled Control |
| HPV47 | 124 | ATGGCGGACGATTCAGGTAC | | >1000 | Sense Control |
| HPV46 (+9 TO +20) | 125 | GTACCTGAATCG | | 200 | |
| HPV41 (+8 TO +20) | 126 | GTACCTGAATCGT | | 365 | |
| HPV42 (+7 TO +20) | 127 | GTACCTGAATCGTC | | 133 | |
| HPV43 (+1 TO +12) | 112 | ATCGTCCGCCAT | | 148 | |
| HPV44 (+1 TO +13) | 128 | AATCGTCCGCCAT | | 138 | |
| HPV45 (+1 TO +14) | 129 | GAATCGTCCGCCAT | | 105 | |
| HPV1 R | 130 | GTACCTGAATCGTCCGCCATc | | | c=rC X=DNA, 3'-ribo cap for ox. |
| HPV1 R Ox. | 130 | GTACCTGAATCGTCCGCCATc(dialdehyde) | | | 3'-ribo /NaIO$_4$ ox. |
| HPV1 R Ox./Red. | 130 | GTACCTGAATCGTCCGCCATc(diol) | | | 3'-ribo /NaIO$_4$ + NaCNBH$_3$ |
| HPV1 R/Spermine | 130 | GTACCTGAATCGTCCGCCATc(spermine) | | | 3'-ribo /NaIO$_4$ + Spermine/NaCNBH$_3$ |
| HPV1 R/Spermidine | 130 | GTACCTGAATCGTCCGCCATc(spermidine) | | | 3'-ribo /NaIO$_4$ + Spermidine/ NaCNBH$_3$ |
| HPV1 T/TAEA | 130 | GTACCTGAATCGTCCGCCATc(TAEA) | | | 3'-ribo / NaIO$_4$ + TAEA/NaCNBH$_3$ (TAEA=Tris(2'-aminoethyl) amine) |

Figure 3:
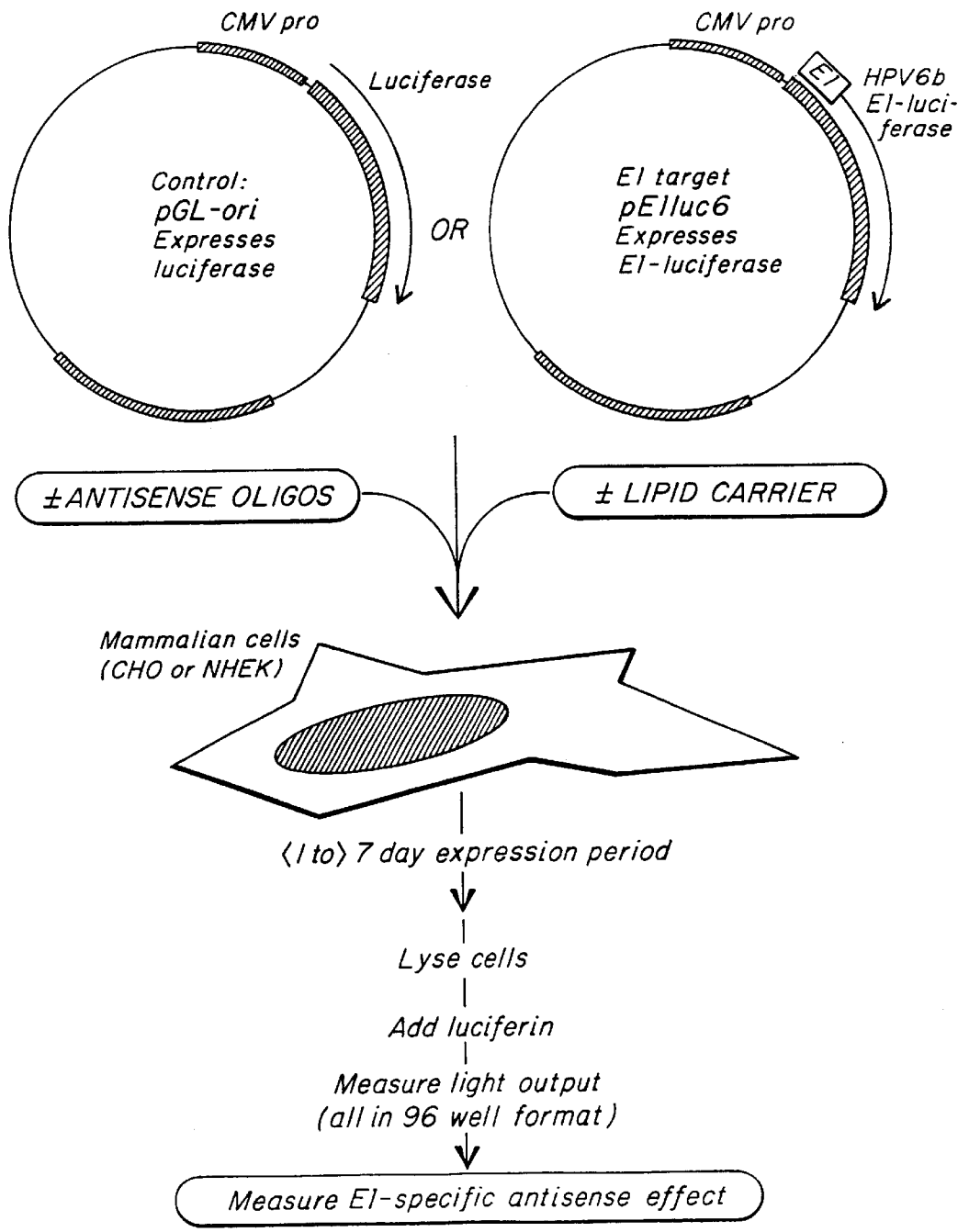
FIG. 3 is a diagrammatic representation of a transiently transfected luciferase assay used to show antisense activity of the oligonucleotides of the invention.

CAPITAL REPRESENTS THE ANTISENSE SEQUENCE
lower case represents non-antisense sequence
Outlined residues are basepaired
<u>Underlined sequence is 2'-OMe RNA</u>
Bold sequence is methylphosphonate
L = non-nucleoside polyethylene glycol (PEG) linker
Internucleotide linkage is PS unless otherwise mentioned Antisense assays with the oligonucleotides of the invention were also performed in transiently transfected CHO cells. Cells were transfected using the lipid carrier, Lipofectamine, either with the plasmid pE1Luc6 or the control plasmid pGLori in the presence of PS oligonucleotides (FIG. 3). Two independent methods of analyzing antisense activity were investigated. In the first, the amount of reporter plasmid was titrated over a 1,000–10,000 fold range in order to determine the linear range of luciferase expression under these assay conditions. Antisense oligonucleotides were added at fixed concentrations to each of these plasmid dilution series, and luciferase activity measured. A decrease in luciferase signal in a plasmid titration curve caused by the addition of oligonucleotide indicates an antisense effect. This protocol was later refined by fixing the concentration of reporter plasmid at an optimum concentration, to carefully titrate the amount of oligonucleotide required to establish a specific antisense effect. This method was used to determine relative luciferase expression as measured in relative luciferase units (see FIGS. 4 and 5) for particular compounds, and also to determine slight differences in activity among them.

Figure 4:
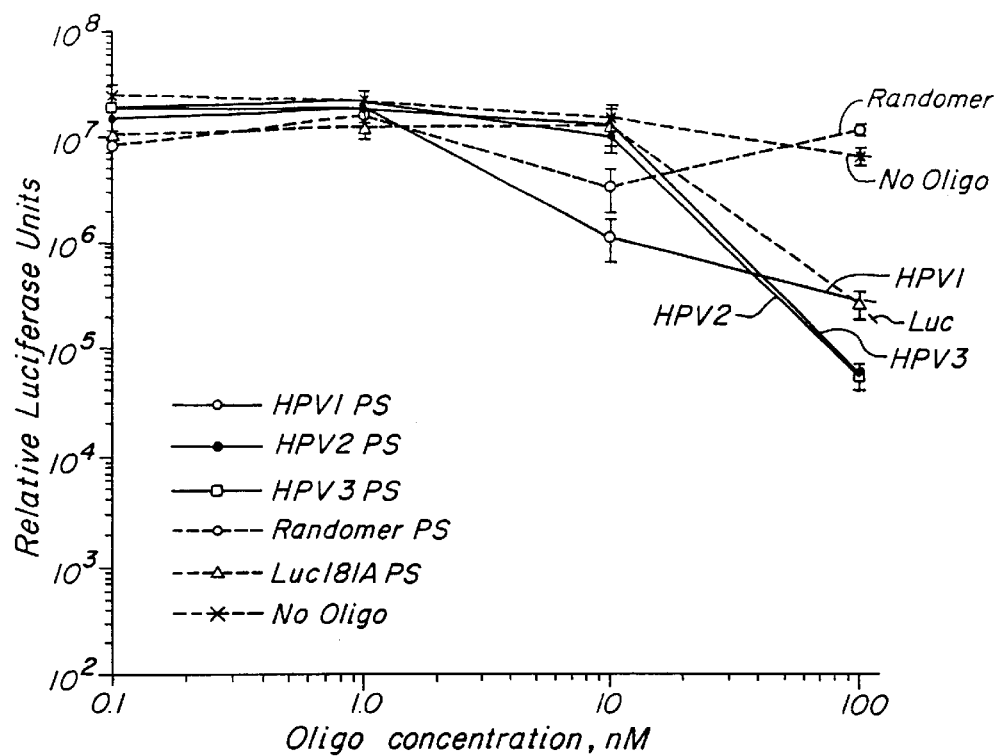
FIG. 4 is a graphic representation showing the antisense inhibition of HPV/luciferase expression in transiently transfected CHO cells treated with different concentrations of PS HPV1, HPV2 or HPV3.
Figure 5:
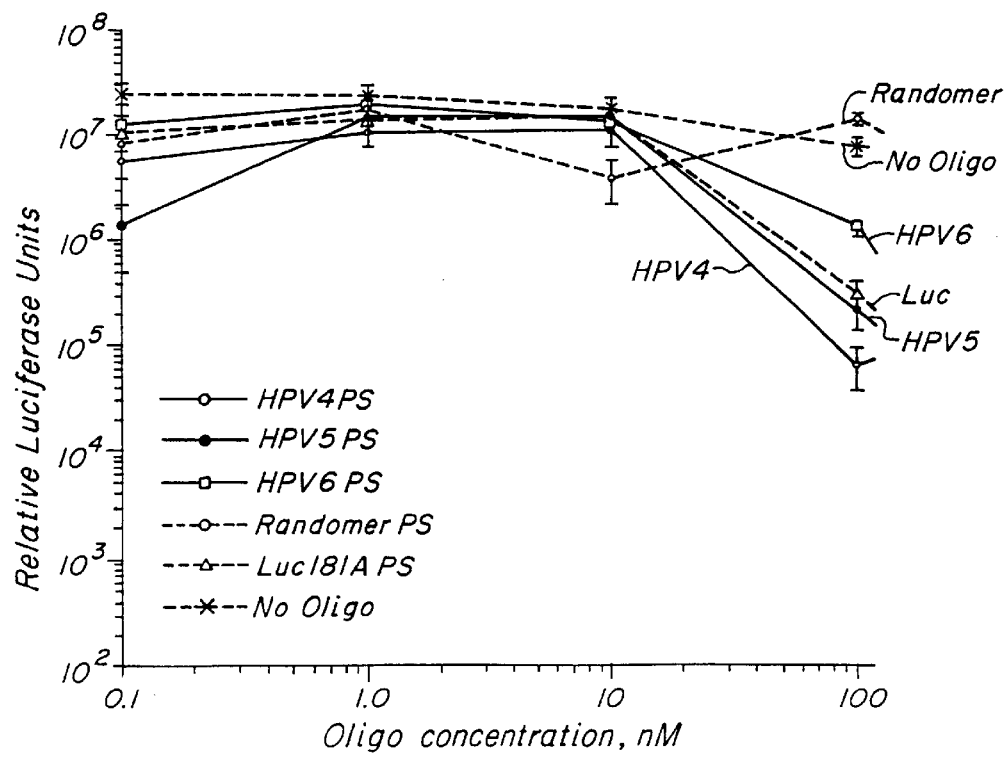
FIG. 5 is a graphic representation showing the antisense inhibition of HPV/luciferase expression in transiently transfected CHO cells treated with different concentrations of PS HPV4, HPV5, and HPV6.

FIGS. 4 and 5 show that phosphorothioate oligonucleotides tested in this region, including HPV1 (SEQ ID NO:1), HPV2 (SEQ ID NO:2), HPV3 (SEQ ID NO:3), HPV4 (SEQ ID NO:4), HPV5 (SEQ ID NO:5), and HPV6 (SEQ ID NO:6), are active antisense compounds. HPV17 (SEQ ID NO:9) was also active in this assay. The randomer negative control produces little effect against both plasmids up to 300 nM. Finally, the Luc +1–+20 positive control compound, which targets both constructs, shows specific antisense activity against both. HPV specific antisense activity occurs at concentrations from less than 1 nM to greater than 300 nM. HPV1 through 6 show similar specific activities against pE1Luc6 (FIGS. 4 and 5). At 100 nM, all compounds specifically reduce E1-luciferase expression by greater than 90% compared to the randomer control. At concentrations greater than 100 nM, randomer oligonucleotides have non-sequence-specific inhibitory effects in the transiently transfected cell system. Accordingly, data are not shown for oligonucleotide concentrations above 100 nM. Against gene expression from the control pGLori plasmid, these compounds show the same effect as the randomer, indicating that they specifically target only the HPV E1 sequence.

HPV24 (SEQ ID NO:29) is a 28 mer variant of HPV17 (SEQ ID NO:9) with a 3' tail, which was designed to fold back to form a stabilizing triplex structure. In the transiently transfected CHO cell assay, this oligonucleotide retained antisense activity. Other similar designed oligonucleotides displayed antisense activity as well (see Table 1B).

Figure 6:
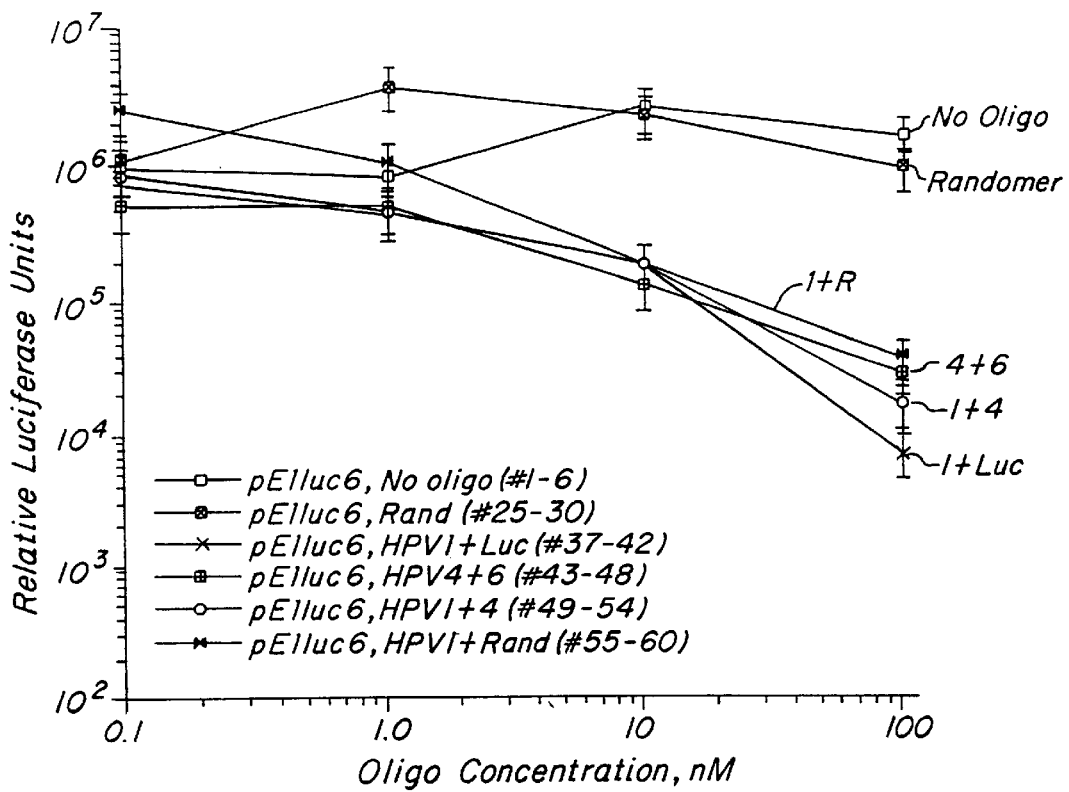
FIG. 6 is a graphic representation showing the antisense inhibition of HPV/luciferase expression in transiently transfected CHO cells treated with a combination of different concentrations of PS HPV1, HPV4, and HPV6.

It may be desirable at times to use a mixture of different oligonucleotides targeting different conserved sites within a given viral gene. Such a mixture of oligonucleotides may be in the form of a therapeutic composition comprising at least one, 2 or more oligonucleotides in a single therapeutic composition (i.e., a composition comprising a physical mixture of at least two oligonucleotides). Alternatively, these oligonucleotides may have two different sequences. For example, various compounds targeting different separate or overlapping regions within the E1-luciferase transcript were mixed, keeping the absolute oligonucleotide concentration constant at 100 nM. FIG. 6 indicates that E1-specific oligonucleotides were active when mixed with other E1-specific oligonucleotides, the randomer, or Luc +1–+20. This indicates that lower concentrations of individual oligonucleotides can be combined to retain a strong specific antisense activity.

Figure 7:
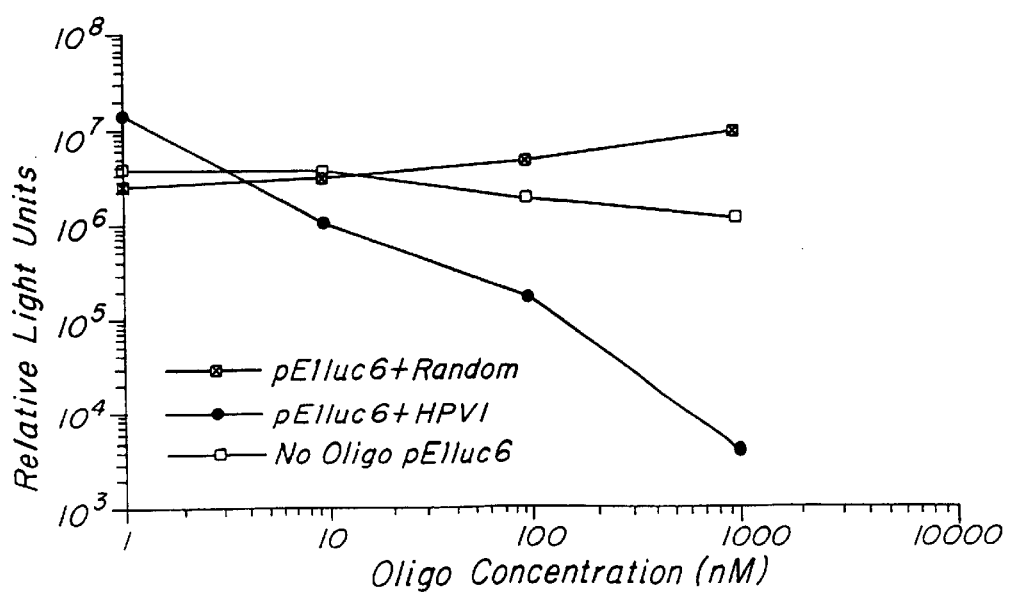
FIG. 7 is a graphic representation showing the effect of different concentrations of HPV1 or random oligonucleotide on the expression of HPV/luciferase in keratinocytes when introduced into the cells via a lipid carrier.

A relevant cell line for assessing antisense activity against HPV is the target cell of the virus, the human keratinocyte. HPV-specific oligonucleotides of the invention were tested in similar transient transfection assays as those described above for CHO cells. The neonatal human epidermal foreskin keratinocytes (NHEK) were transiently transfected with either pE1Luc6 or pGLori using the lipid carrier, Lipofectamine. PS oligonucleotides were added to the cells in the presence of lipid carrier. The results shown in FIG. 7 demonstrate that in the presence of randomer oligonucleotide or in the absence of any oligonucleotide the levels of luciferase expression in the keratinocytes are high (between $10^6$ and $10^7$ relative light units (RLU) in each well). The randomer does not cause any observable non-specific effects in cells transfected with either of the two reporter plasmids, pE1Luc6 or pGLori. The HPV1 oligonucleotide added in the presence of Lipofectamine to cells transfected with pE1Luc6 decreased luciferase expression to $2 \times 10^4$ RLU at a concentration of 100 nM, demonstrating a sequence-specific effect. A similar effect was seen when the oligonucleotides were added in the absence of lipid carrier.

Thus, in these experiments an oligonucleotide-specific decrease in reporter plasmid expression can be demonstrated in normal human keratinocytes when the oligonucleotides are delivered into the cells with a lipid carrier.

Activity of the oligonucleotides of the invention may be verified in three dimensional epithelia cultured in vitro. This involves placing HPV positive keratinocytes on a collagen membrane (collagen raft) and culturing the cells at the air-liquid interface. The keratinocytes that are used in these experiments may be derived from normal neonatal foreskins or obtained from Condylomata acuminata biopsy material. These collagen raft (organotypic) cultures encourage the keratinocytes to differentiate and form a three-dimersional structure which mimics that found in vivo. This ordered process of normal cellular differentiation may permit the papillomavirus to undergo vegetative replication, a process which requires the replication of the viral genome within the cell. Antisense oligonucleotides are added to the culture medium below the raft. As occurs in vivo, oligonucleotides must be taken up by the keratinocytes and reach the cells where active viral DNA replication is taking place in order to abrogate this process. The effect of antisense oligonucleotides on the HPV life cycle may be monitored by visualizing the viral load in each raft culture using in situ hybridization with probes for HPV DNA. This process may be quantified by image analysis. In addition, if riboprobes specific for individual viral open reading frames are used, expression of individual viral genes may be demonstrated and the possible mode of action of the antisense oligo may be determined. A conventional immunohistochemical analysis of the collagen raft cultures is also used to demonstrate the expression (or lack thereof) of viral proteins. In addition, classical histology coupled with immunohistochemistry is also used to demonstrate a correlation between an active papillomavirus infection, atypical cell histology and aberrant cellular differentiation.

Figure 8:
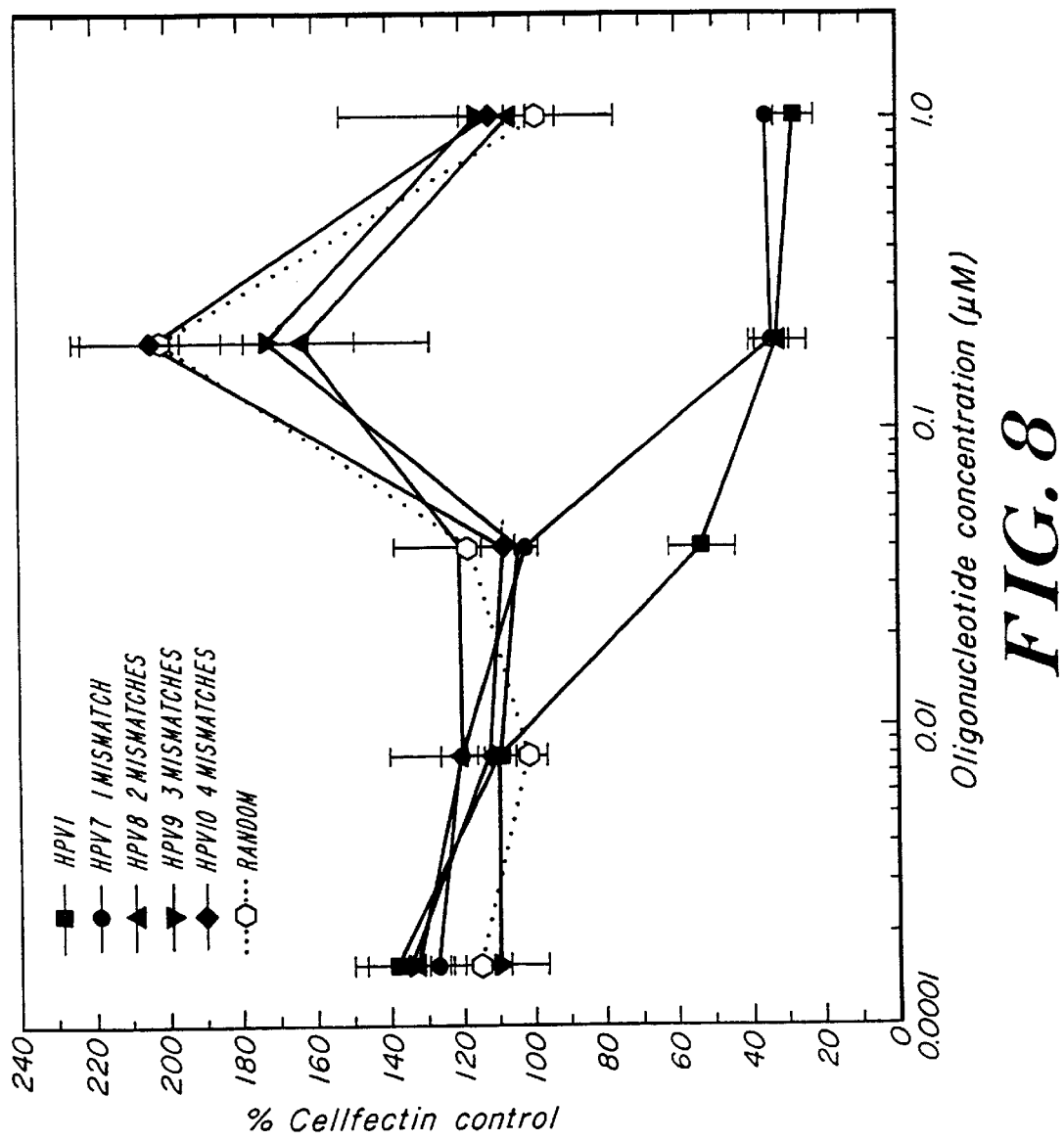
FIG. 8 is a graphic representation of the antisense activity in the stably transfected CHO cell assay of oligonucleotides with base mismatches.
Figure 9:
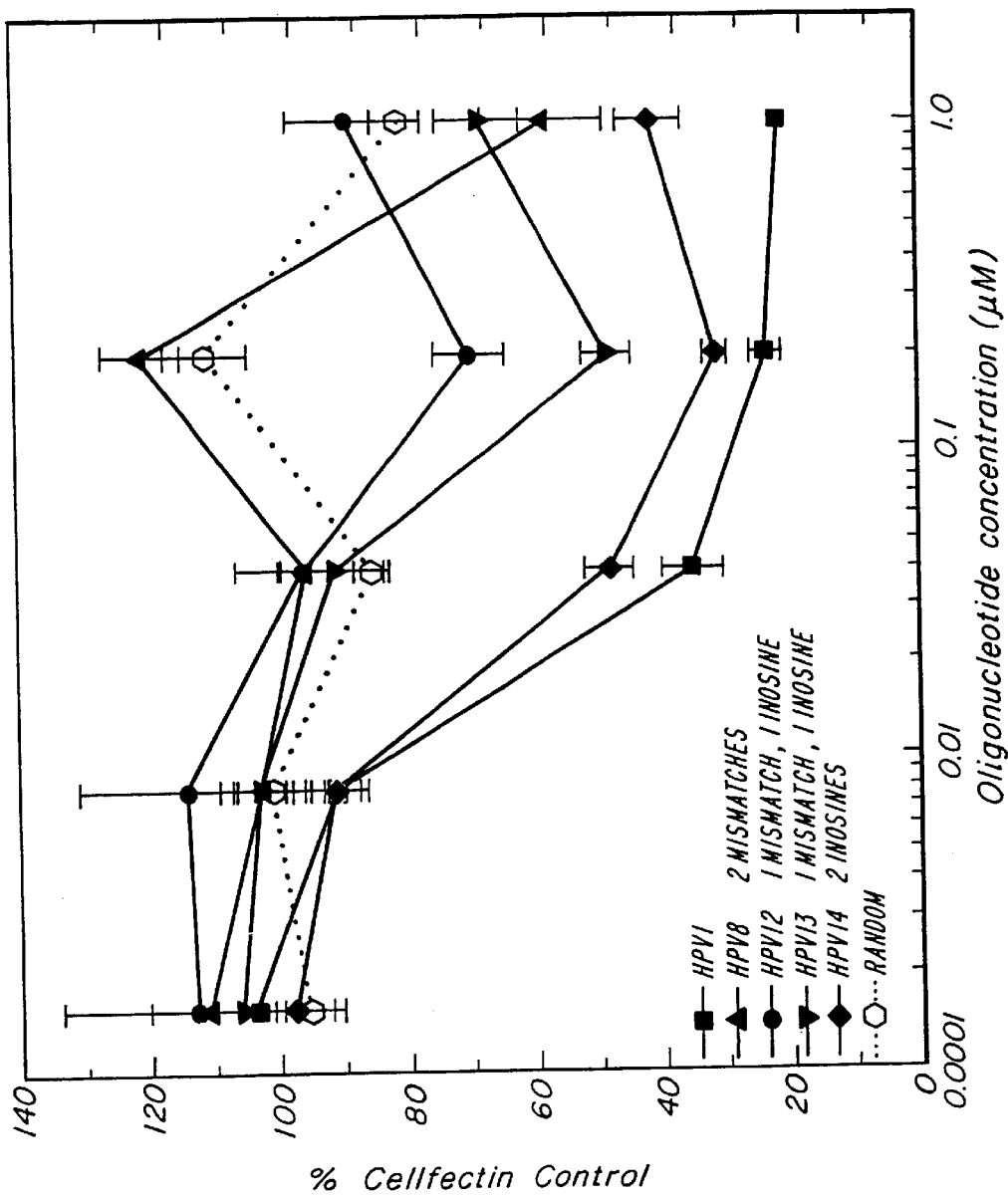
FIG. 9 is a graphic representation of the antisense activity in the stably transfected CHO cell assay of oligonucleotides with base mismatches and oligonucleotides with mismatches replaced with inosines.
Figure 10A:
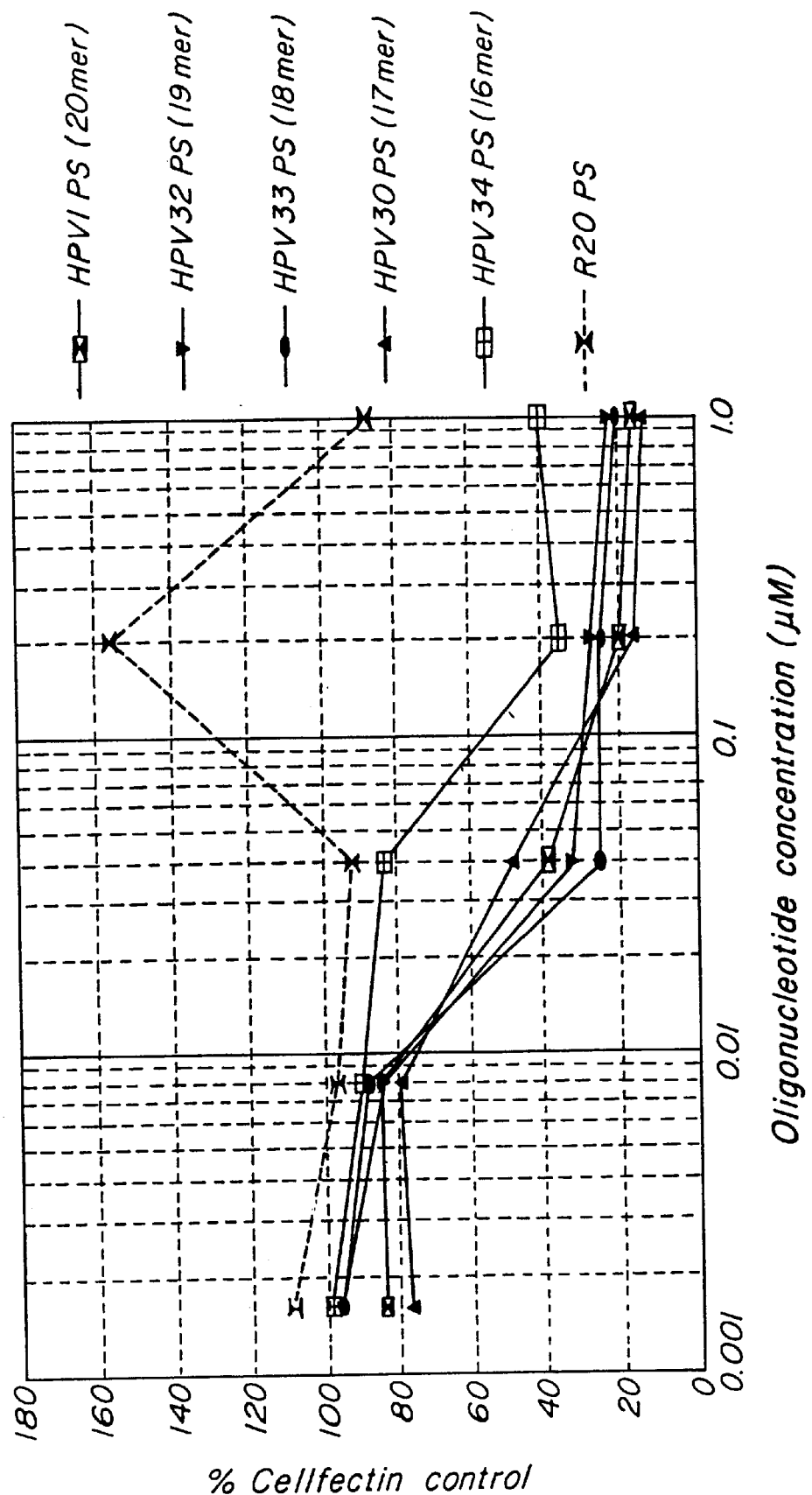
FIG. 10A is a graphic representation showing the antisense activity of HPV1, HPV32, HPV33, HPV30, and HPV34 in the stably transfected CHO cell assay.
Figure 10B:
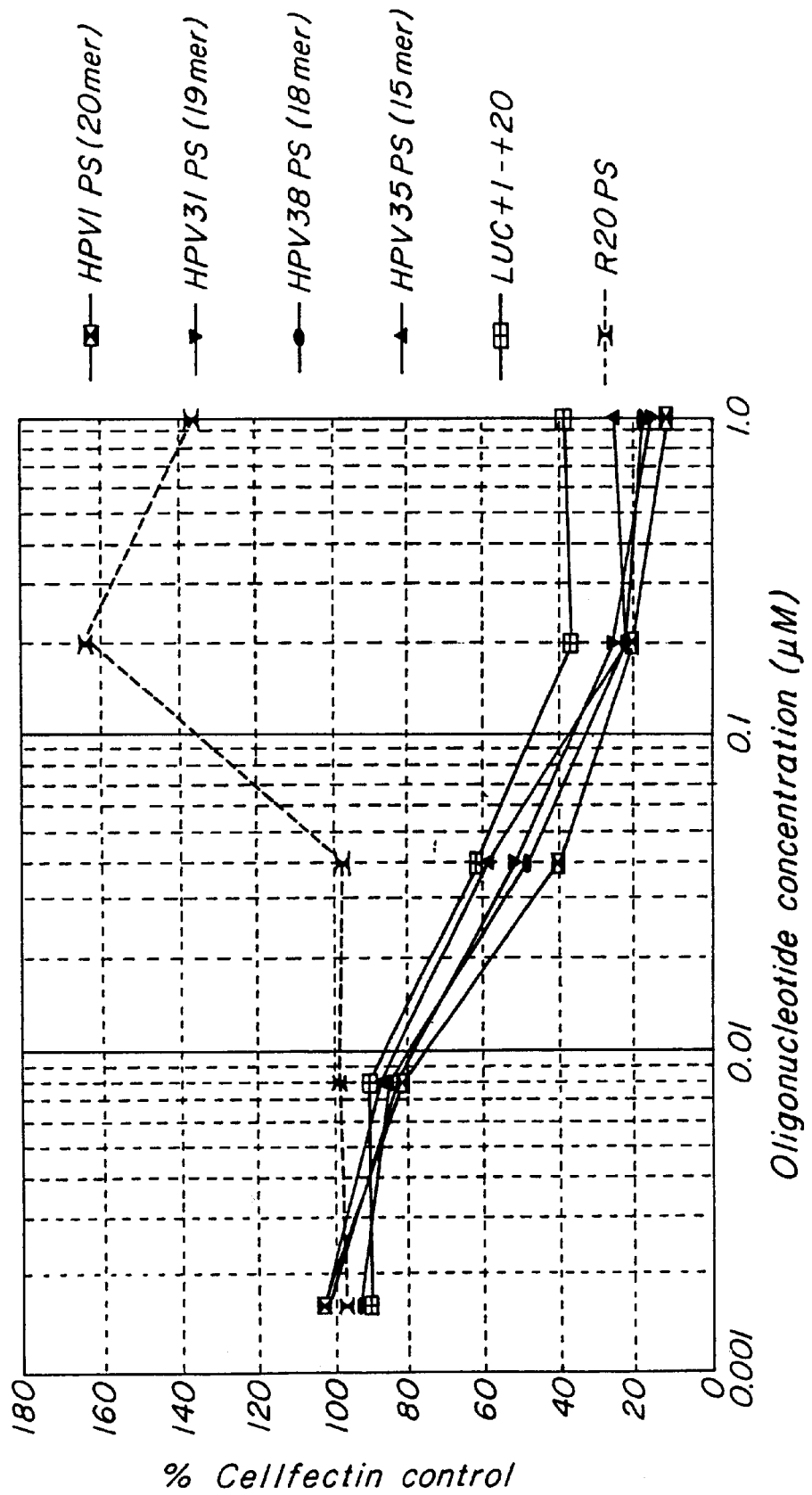
FIG. 10B is a graphic representation showing the antisense activity of HPV1, HPV31, HPV38, and HPV35 in the stably transfected CHO cell assay.
Figure 11:
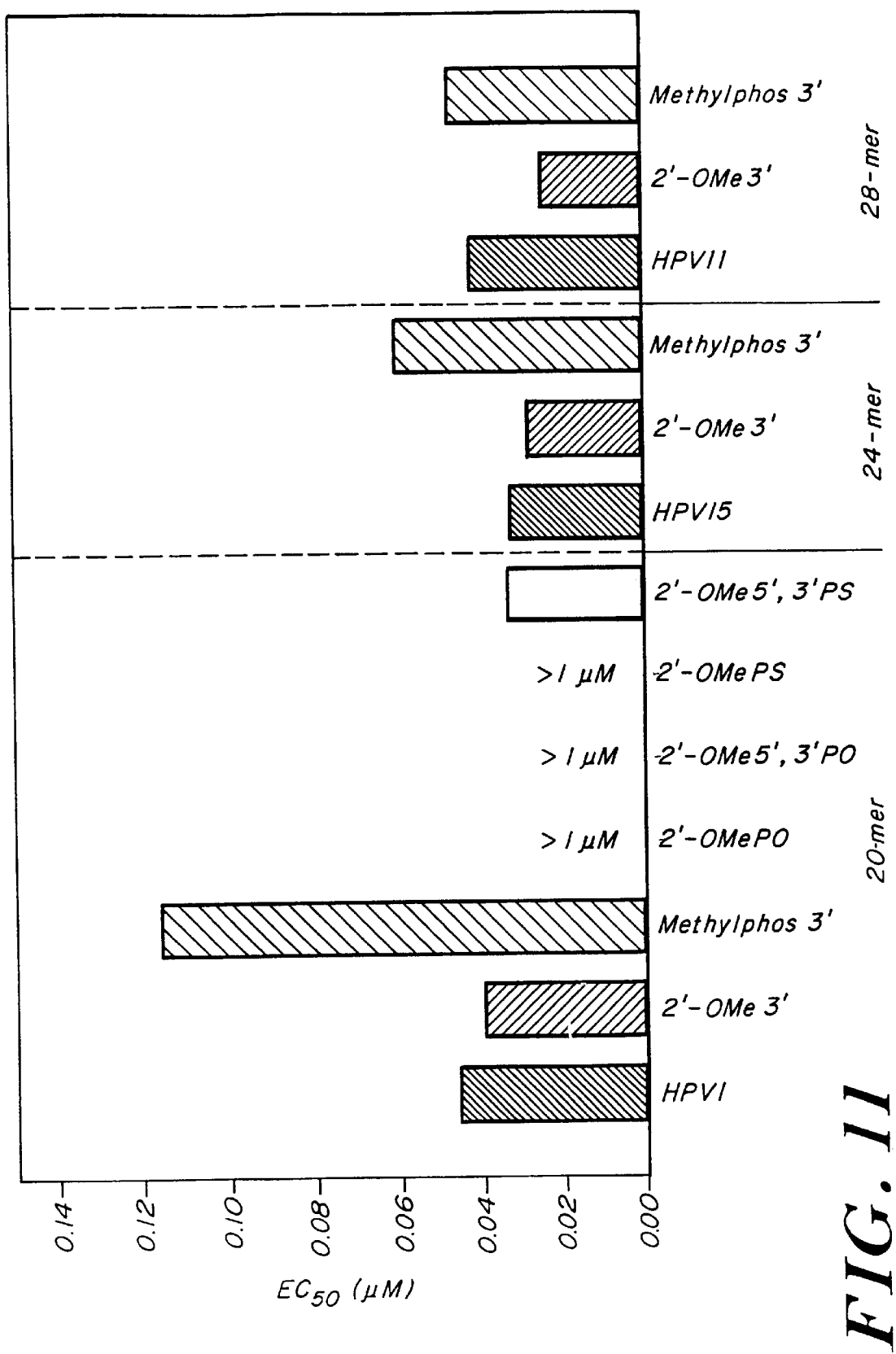
FIG. 11 is a graphic representation of the effects of length and chemical modification on the antisense activity in stably transfected cells, where HPVn=phosphorothioate (PS); 2' OMe 3'=3' end 5 nucleotide 2'-O-methyl RNA PS modification; methylphos 3'=3' end 5 nucleoside methylphosphonate modification; 2' OMe PO or PS=all 2'-O-methyl RNA phosphodiester or phosphorothioate; 2' OMe 5', 3' PO or PS=5 nucleotide 2'-O-methyl RNA PO/PS modification at both 5' and 3' ends.

To determine whether oligonucleotides of the invention had true sequence-specific antisense activity, an increasing number of mismatches were introduced into the HPV1 sequence: the G residues were sequentially mutated to A (see Table 1A in which the lower case letters in HPV7–10, 12–14, and 29 show the locations of mismatches relative to the target sequence). Using the CHO-K1 cells stably transfected with the E1Luc6 construct, it was shown that one mismatch did not noticeably effect sequence specific antisense activity, but that two or more mismatches abrogated the activity of HPV1 (SEQ ID NO:1) (FIG. 8). This correlated with the RNase H cleavage efficiency of the oligonucleotides shown in Table 1A. HPV7 (SEQ ID NO:31) with one base mismatch had no effect on RNase H cleavage, but two mismatches (HPV8, SEQ ID NO:32) reduced RNase H cleavage by 50%, and three mismatches (HPV9, SEQ ID NO:33) essentially Eliminates RNase H activity. Similar results were seen in the transiently transfected CHO cell system.

In order to design a compound which will be effective against many clinical isolates of HPV, it is essential to chose a well-conserved region of E1. However, base mismatches are likely to be present in antisense oligonucleotides targeted against more than one HPV type, and two base mismatches can abrogate the antisense activity of HPV1 (see FIG. 8). A solution to the problem of sequence variation is to design oligonucdeotides which can bind to multiple sequences. An oligonucleotide has been designed in which mismatches are replaced by inosine nucleosides (HPV12–14, Table 1A, FIG. 9, where the "i" in oligonucleotides HPV12–14 shows where the mismatched bases were substituted with inosine residues). Inosine forms hydrogen bonds with all normal bases to varying degrees. In the stably transfected assay system, replacement of one or the other of the mismatches in HPV8 (SEQ ID NO:32) with inosine partially restored antisense activity (FIG. 9). Replacement of both mismatches with inosine however restored antisense activity to nearly that of HPV1. Again this correlates with the RNase H cleavage data, as shown in Table 1A. In the presence of two mismatches (HPV8, SEQ ID NO:32) the cleavage efficiency decreased to 52% of that of HPV1. Replacing the most 5' (in the oligo) mismatch with an inosine (HPV12, SEQ ID NO:36) increased the cleavage to 61% of HPV1. Replacing only the most 3' mismatch with inosine (HPV13, SEQ ID NO:37) was more effective in decreasing the effects of the mismatch, raising the cleavage to 76% of HPV1. Replacement of both the mismatches with inosine (HPV14, SEQ ID NO:38) increased the cleavage still further to 81% of HPV1. This demonstrates that placing inosine at the sites of differences between strains allows the oligonudeotides to retain their activity against several strains of HPV. Similar results were seen when comparing HPV8 to HPV14 in transiently transfected CHO cells.

The relationship between oligonucleotide length and activity was also examined. Increasing the length of 20 mer HPV1 at its 3' end to a 24 mer (HPV15, SEQ ID NO:8) or a 28 mer (HPV1, SEQ ID NO:7) did not effect the antisense activity of the oligonucleotide as measured in the stably or transiently transfected CHO-K1 luciferase assays. In addition, sequential deletion of bases from the 5' or 3' end of HPV1 (HPV3039, Table 1A) showed that antisense activity was retained even when four bases had been deleted from the 5' end (FIG. 10A) and when five bases had been deleted from the 3' end (FIG. 10B) in the stably transfected CHO cell system.

The effects of chemical modifications on the antisense activity were also examined. Several different chemical modifications were studied: 5 nucleotides at the 3' end containing methylphosphonate or 2'-O-methyl RNA chemical modifications; 5 nucleotides at the 5' and 3' ends containing 2'-O-methyl RNA chemical modifications; and full length 2'-O-methyl PO and PS oligonucleotides.

FIG. 12 summarizes the data for the different chemical modifications as assayed in the stably transfected CHO-K1 cells. Introduction of five 2'-O-methyl RNA chemical modifications at the 3' end or both the 3' and 5' ends of the sequence appears to increase activity of the 20 mer PS HPV1, while similar methylphosphonate modifications reduced the activity of the 20 mer PS HPV1. Longer oligonucleotides improved the activity of 3' end methylphosphonate modifications. Oligonucleotides having a complete 2'-O-methyl RNA backbone, with either PO or PS linkages, were inactive, which is supportive of the role of RNase H in the antisense activity. Compounds having an n-butyl phosphoramidate backbone, 5 n-butyl phosphoramidates at the 3' end, or a mixed n-butyl phosphoramiate and 2'-O-methyl RNA structure are expected to be active somewhere between the activity of the phosphorothioate and methylphosphonate compounds.

The 2'-O-methyl RNA phosphorothioate hybrid oligonucleotides had even greater activity than deoxyribose phosphorothioates, and regardless of oligonucleotide length, each hybrid oligonucleotide was more active than its corresponding homogeneous phosphorothioate oligonucleotide. The 2'-O-methyl RNA-phosphorothioate mixed backbone version of HPV1 was more active than the phosphorothioate compound in similar transiently transfected CHO cell assays, and methylphosphonate HPV1 retained antisense activity.

Experiments with mixed backbone chemistries were repeated with oligonucleotides of varying lengths, to determine if an increase in length could alter compound activity. Therefore, two longer versions of HPV1 (a 20 mer) were examined in three backbone chemistries (PS, M, and OMe) in transiently transfected CHO cells. For the 24 mer (HPV15), the PS compound showed good antisense activity. The 2'-O-methyl-RNA compound was similarly active; the methylphosphonate backbone was slightly less active. When these modifications were incorporated into a 28 mer oligonucleotide (HPV11), similar results were observed.

Since the results demonstrated similar or improved activity of chimeric and hybrid oligonucleotides after 24 hour cellular incubation times, the antisense effects of these oligonucleotides were studied over longer time periods. The modified oligonucleotides possess increased resistance to degradation in serum, which could translate into extended activity in the cells. In the transiently transfected CHO cell assay, the phosphorothioate compound showed a loss of activity from day 1 to day 7. In contrast, the 2'-O-methyl RNA-phosphorothioate hybrid retained high activity through day 7. Similar results were seen when 24 mers and 28 mers were evaluated.

In conclusion, the combination of chimeric backbone chemistries and phosphorothioate linkages (which mediate cellular RNase H activity), and modifications at the 3' and/or 5' termini, retained antisense efficacy against E1 expression for one week after administration to cells.

To test the toxicity of the oligonucleotides of the invention, a commercially available cytotoxicity assay (CellTiter 96 Non-Radioactive Cell Proliferation/Cytotoxicity Assay, Promega, Madison, Wis.), was used. Compound toxicity was measured in parallel with antisense activity, using the standard transient cell transfection assay system. Regardless of backbone chemistry, oligonucleotides of the invention were not toxic to cells at concentrations where specific antisense activity is observed.

Another assay by which to demonstrate antisense effects against the native biochemical function of the viral E1 gene measures the ability of this protein to stimulate DNA replication initiated at the HPV origin of replication. Papillomavirus DNA replication in mammalian cells requires only three viral components, the E1 and E2 gene products, and a DNA sequence containing the HPV origin of replication. To measure antisense activity against E1 gene expression, two plasmids are constructed which express either E1 or E2 from a CMV promoter. These two plasmids can be targeted with oligonucleotides binding anywhere within the E1 or E2 transcripts. As a reporter for this E1 activity, a plasmid is constructed expressing luciferase, and which in addition contains the HPV type 6 origin of replication. When transfected into a mammalian cell, the copy number of this plasmid increases if E1 and E2 proteins are present; as a result, cellular luciferase expression increases. This increase in enzyme activity can be quantified in a luminometer, and the overall viral DNA replication effect determined. A similar luciferase expression plasmid lacking the HPV origin can be created, which therefore serves as a negative control for these experiments. This plasmid is not affected by expression of viral E1 and E2 genes, and luciferase expression remains constant.

The synthetic antisense oligonucleotides of the invention may be in the form of a therapeutic composition or formulation useful in inhibiting HPV replication in a cell, and in treating human papillomavirus infections and associated conditions in an animal, such as skin and genital warts, epidermodysplasia verruciformis, respiratory or laryngeal papillomatosis, or cervical carcinoma. They may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of HPV expression. For example, combinations of synthetic oligonucleotides, each of which is directed to a different region of the HPV nucleic acid, may be used in the pharmaceutical compositions of the invention. The pharmaceutical composition of the invention may further contain other chemotherapeutic drugs for the treatment of cervical carcinoma. Such additional factors and/or agents may be included in the pharmaceutical composition to produce a synergistic effect with the synthetic oligonucleotide of the invention, or to minimize side-effects caused by the synthetic oligonudeotide of the invention. Conversely, the synthetic oligonucleotide of the invention may be included in formulations of a particular anti-HPV or anti-cancer factor and/or agent to minimize side effects of the anti-HPV factor and/or agent.

The pharmaceutical composition of the invention may be in the form of a liposome in which the synthetic oligonucleotides of the invention are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. The pharmaceutical composition of the invention may further include other lipid carriers, such as Lipofectamine, or cyclodextrins and the like which enhance delivery of oligonucleotides into cells, or such as slow release polymers.

As used herein, the term "therapeutically effective amount" means the total amount of each active component of the pharmaceutical composition or method that is sufficient to show a meaningful patient benefit, i.e., a reduction in the number and size of skin and genital warts, a reduction in epidermodysplasia verruciformis, respiratory or laryngeal papillomatosis, or remission of cervical carcinoma. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one or more of the synthetic oligonucleotides of the invention is administered to a subject afflicted with an HPV-associated disease. The synthetic oligonucleotide of the invention may be administered in accordance with the method of the invention either alone or in combination with other known therapies for the HPV-associated disease. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

It may be desirable at times to use a mixture of different oligonucleotides targeting different conserved sites within a given viral gene. Such a mixture of oligonucleotides may be in the form of a therapeutic composition comprising at least one, 2 or more oligonucleotides in a single therapeutic composition (i.e., a composition comprising a physical mixture of at least two oligonucleotides). Alternatively, these oligonucleotides may have two different sequences at times. At least one, preferable two or more oligonucleotides may be administered simultaneously or sequentially as a single treatment episode in the form of separate pharmaceutical compositions.

Administration of the synthetic oligonucleotide of the invention used in the pharmaceutical composition or to practice the method of treating an animal can be carried out in a variety of conventional ways, such as intraocular, oral ingestion, inhalation, or cutaneous, subcutaneous, intramuscular, or intravenous injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, cutaneous or subcutaneous injection, the synthetic oligonucleotide will be in the form of a pyrogen-free, parenterally acceptable aqueous solution. The preparation of such parenterally acceptable solutions, having due regarding to pH, isotonicity, stability, and the like, is within the skill in the art. A preferred pharmaceutical composition for intravenous, cutaneous, or subcutaneous injection should contain, in addition to the syntheic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patient has undergone. Ultimately, the attending physician will decide the amount of synthetic oligonucleotide with which to treat each individual patient. Initially, the attending physician will administer low doses of the synthetic oligonucleotide and observe the patient's response. Larger does of synthetic oligonucleotide may be administered until the optimal therapeutic effect is obtained for the patient, and at that point the dosage is not increased further. It is contemplated that the various pharmaceutical compositions used to practice the method of the present invention should contain about 1.0 ng to about 2.5 mg of synthetic oligonucleotide per kg body weight.

The duration of intravenous therapy using the pharmaceutical composition of the present invention will vary, depending on the severity of the disease being treated and the condition and potential idiosyncratic response of each individual patient. It is contemplated that the duration of each application of the synthetic oligonucleotide will be in the range of 12 to 24 hours of continuous intravenous administration. Ultimately the attending physician will decide on the appropriate duration of intravenous therapy using the pharmaceutical composition of the present invention.

The oligonucleotides of the invention may also be a part of kits for inhibiting human papillomavirus replication and infection in a cell. Such a kit includes a synthetic oligonucleotide specific for HPV nucleic acid, such as those described herein. For example, the kit may include at least one of the synthetic contiguous oligonucleotides of the invention, such as, but not limited to, those having SEQ ID NO: 1–39. These oligonucleotides may have modified backbones, such as those described above, and may be RNA/DNA hybrids containing, for example, at least one 2'-O-methyl. The kit of the invention may optionally include buffers, cell or tissue preparation reagents, cell or tissue preparation tools, vials, and the like.

Other kits of the invention are for detecting the presence of HPV in a sample, such as a solution or biological sample, such as a fluid, tissue, tissue homogenate, and the like. These kits contain at least one synthetic oligonucleotide complementary to a nucleic acid spanning the translational start site of human papillomavirus E1 gene, and means for detecting the oligonucleotide hybridized with the nucleic acid if HPV is present in the sample.

The following examples illustrate the preferred modes of making and practicing the present invention, but are not meant to limit the scope of the invention since alternative methods may be utilized to obtain similar results.

EXAMPLES

1. RNase H Assay

A. Linearization of DNA Template

The E1 gene from plasmid pE16B1 was subcloned by polymerase chain reaction into the vector PCR-Script (Stratagene, La Jolla, Calif.). The PCR-pE16B1 plasmid (20 µg) was linearized with NotI restriction enzyme (New England Biolabs, Beverly, Mass., 60 U) for 4 hours at 37° C., treated with proteinase K (Stratagene, La Jolla, Calif.) (0.1 µg/µl) for 1 hour at 37° C. and twice phenol/chloroform extracted. The linearized plasmid was ethanol precipitated and isolated from the supernatant by centrifugation. The dried pellet was dissolved in diethylpyrocarbonate (Aldrich, Milwaukee, Wis.)-treated water to a concentration of 0.5 µg/µl.

B. In Vitro Transcription and $^{32}$P-Labelling of HPV RNA

HPV E1 mRNA was transcribed in vitro using the Stratagene mRNA Transcription Kit (La Jolla, Calif.), and the manufacturer's T7 RNA polymerase supplied with the kit. Transcription was performed in the presence of 7.5 mM CTP, 7.5 mM ATP, 75 mM UTP, 6 mM GTP, and 6 mM guanosine hydrate. The reduced GTP concentration allowed the initiation of a high percentage of the transcripts with guanosine to facilitate end-labelling of the RNA without pretreatment with alkaline phosphatase. After transcribing for 3 hours at 37° C., the reaction was treated with RNase-free DNase (Stratagene, La Jolla, Calif. or Ambion, Austin, Tex.), twice phenol/chloroform extracted, and chromatographed through a G-50 Sephadex spin-column (Boehringer-Mannheim, Indianapolis, Ind. or Pharmacia, Uppsala, Sweden) to remove unreacted nucleotides and nucleoside. The recovered RNA was quantitated by measuring the UV absorbance at 260 nm using an extinction coefficient of 10000 $^{-1}$ cm$^{-1}$ base$^{-1}$ of the RNA.

The RNA (5 µg) was end-labelled with 20–25 units of T4 polynucleotide kinase (Pharmacia, Uppsala, Sweden) and 50 µCi Y-$^{32}$P]ATP (Amersham, Arlington Heights, Ill.), 6000 Ci/mmol). The labelled RNA was purified by chromatography through a G-50 Sephadex spin column (Boehringer-Mannheim, Indianapolis, Ind., or Pharmacia, Uppsala, Sweden).

C RNase H Cleavage with Random 20 mer Library

End-labelled RNA (20–100 nM) was incubated with a 20 base random DNA library (50–100 µM) (synthesized on Pharmacia Gene Assembler, as described below), boiled previously to dissociate any aggregates, for 90 min at 37° C. in 9 µl 1× buffer (40 mM Tris-HCpH 7.4,4 mM MgCl$_2$, 1 mM DTT). RNase H (Boehringer-Mannheim, Indianapolis, Ind.) (1 µl, 1 unit/µl) was then added. The reaction was incubated at 37° C. for 10 min, quenched by addition of 10 µl 90% formamide containing 0.1% phenol red/0. 1% xylene cyanol, and frozen on dry ice. The quenched reactions were boiled for 2.5 to 3 minutes, quenched on ice, and 5 to 7 µl loaded onto a denaturing 4% polyacrylamide gel prerun to 50 to 55° C. The phenol red was typically run to the bottom of the gel, which was then dried at 80° C. under vacuum. The gel was autoradiographed using XOMAT film (Kodak, Rochester, N.Y.) or analyzed using phosphorimage technology on a Molecular Dynamics (Sunnyvale, Calif.) or Bio Rad Phosphorimager (Hercules, Calif.).

D. Cleavage of HPV RNA with Specific Antisense Oligonucleotides

In 9 µl 1× RNase H buffer (40 mM Tris-HCl pH 7.4, 4 mM MgCl$_2$, 1 mM DTT), 20–100 nM [5'-$^{32}$P]-labelled RNA and 100 nM oligonucleotides (ODN) were preincubated for 15 min at 37° C. 1 µl RNase H (1 U/µl ) was added, and the reaction was incubated at 37° C. for 10 min. The reactions were quenched and analyzed as described above. Quantitation of the cleavage products was performed using software supplied with the PhosphorImager (Molecular Dynamics, Sunnyvale, Calif., or Bio-Rad Laboratories, Hercules, Calif.). "Counts" were determined by drawing a box around the band of interest and subtracting the background determined with a box drawn nearby. Counts in a product band were compared to total counts in the lane above that band to determine percent cleavage.

E. Cleavage of HPV mRNA with Semirandom Oligonucleotides

Semirandom oligonucleotides (100 µM in H$_2$O) are boiled for 1 min to dissociate any aggregates formed between complementary sequences in the mix and 1 µl (final concentration 10 µM) is added to 8 µl 1× RNase H buffer (40 mM Tris-HCl pH 7.4, 4 mM $MgCl_2$, 1 mM DTT) containing labelled mRNA (20–100 nM). After a 15 minute preincubation at 37° C., RNase H is added (1 U) and incubated for 10 min at 37° C. The reactions are quenched and analyzed as described above. Sites of cleavage are estimated using DNA and/or RNA molecular size markers.

2. Synthesis of Oligonucleotides

Oligonucleotides were synthesized using standard phosphoramidite chemistry (Beaucage (1993) Meth. Mol. Biol. 20:33–61) on either an ABI 394 DNA/RNA synthesizer (Perkin-Elmer, Foster City, Calif.), a Pharmacia Gene Assembler Plus (Pharmacia, Uppsala, Sweden) or a Gene Assembler Special (Pharmacia, Uppsala, Sweden) using the manufacturers' standard protocols and custom methods. The custom methods served to increase the coupling time from 1.5 min to 12 min for the 2'-O-methyl RNA amidites. The Pharmacia synthesizers required additional drying of the amidites, activating reagent and acetonitrile. This was achieved by the addition of 3 Å molecular sieves (EM Science, Gibbstown, N.J.) before installation on the machine.

DNA β-cyanoethyl phosphoramidites were purchased from Cruachem (Glasgow, Scotland). The DNA support was 500 Å pore size controlled pore glass (CPG) (PerSeptive Biosystems, Cambridge, Mass.) derivatized with the appropriate 3' base with a loading of between 30 to 40 mmole per gram. 2'-O-methyl RNA β-cyanoethyl phosphoramidites and CPG supports (500 A) were purchased from Glen Research (Sterling, Va.). For synthesis of random sequences, the DNA phosphoramidites were mixed by the synthesizer according to the manufacturer's protocol (Pharmacia, Uppsala, Sweden).

All 2'-O-methyl RNA-containing oligonucleotides were synthesized using ethylthiotetrazole (American International Chemical (AIC), Natick, Mass.) as the activating agent, dissolved to 0.25 M with low water acetonitrile (Aldrich, Milwaukee, Wis.). Some of the DNA-only syntheses were done using 0.25 M ethylthiotetrazole, but most were done using 0.5 M 1-H-tetrazole (AIC). The thiosulfurizing reagent used in all the PS oligonucleotides was 3H-1,2-benzodithiol-3-one 1,1-dioxide (Beaucage Reagent, R.I. Chemical, Orange, Calif., or AIC, Natick, Mass.) as a 2% solution in low water acetonitrile (w/v).

The cholesteryl CPG (chol) and polyethylene glycol (PEG), 5'-amino-modifier [$C_6NH_2$] and cholestryl (chol) phosphoramidites used to synthesize oligos with such linkers as described in Table 1B were used in accordance with manufacturer's instructions (Glen Research, Sterling, Va.).

The 3'-$NH_2$ Cap is a 3'-(3-amino 2-propanol) conjugate (Table 1B) which was prepared with 3'-amino modifier C3 CPG according to manufacturer's instructions (Glen Research, Sterling, Va.).

For oxidation, Redox or amination of oligonucleotide phosphorothioates containing a ribonucleotide at the 3' terminus (Table 1B) the synthesis was carried out as follows. Oligonucleotide phosphorothioate (1 mM) containing a ribonucleotide at the 3' terminus was oxidized with $NaIO_4$ (1.2 mM) for 30 minutes on ice in 0.1 M sodium acetate pH 4.75 to yield the 3'-dialdehyde (Ox.) product. For addition of amines, 6 equivalents of amine in 0.2 M sodium phosphate buffer (pH 8) was added to the oxidized oligonucleotide at room temperature for 30 minutes followed by addition of 30 equivalents of $NaCNBH_3$. The solution was left overnight at room temperature. The product was purified by preparative polyacrylamide gel Electrophoresis on a 20% denaturing gel. The same procedure was carried out in the absence of amine to yield the 3' diol (Ox/Red.) product.

After completion of synthesis, the CPG was air dried and transferred to a 2 ml screw-cap microfuge tube. The oligonucleotide was deprotected and cleaved from the CPG with 2 ml ammonium hydroxide (25–30%). The tube was capped and incubated at room temperature for 20 minutes, then incubated at 55° C. for 7 hours. After deprotection was completed, the tubes were removed from the heat block and allowed to cool to room temperature. The caps were removed and the tubes were microcentrifuged at 10,000 rpm for 30 minutes to remove most of the ammonium hydroxide. The liquid was then transferred to a new 2 ml screw cap microcentrifuge tube and lyophilized on a Speed Vac concentrator (Savant, Farmingdale, N.Y.). After drying, the residue was dissolved in 400 μl of 0.3 M NaCl and the DNA was precipitated with 1.6 ml of absolute EtOH. The DNA was pelleted by centrifugation at 14,000 rpm for 15 minutes, the supernatant decanted, and the pellet dried. The DNA was precipitated again from 0.1 M NaCl as described above. The final pellet was dissolved in 500 μl $H_2O$ and centrifuged at 14,000 rpm for 10 minutes to remove any solid material. The supernatant was transferred to another microcentrifuge tube and the amount of DNA was determined spectrophotometrically. The concentration was determined by the optical density at 260 nM. The $E_{260}$ for the DNA portion of the oligonucleotide was calculated by using OLIGSOL (Lautenberger (1991) *Biotechniques* 10:778–780). The $E_{260}$ of the 2'-O-methyl portion was calculated by using OLIGO 4.0 Primer Extension Software (NBI, Plymouth, Minn.).

Oligonucleotide purity was checked by polyacrylamide gel Electrophoresis (PAGE) and UV shadowing. 0.2 $OD_{260}$ units were loaded with 95% formamide/$H_2O$ and Orange G dye onto a 20% denaturing polyacrylamide gel (20 cm×20 cm). The gel was run until the Orange G dye was within one inch of the bottom of the gel. The band was visualized by shadowing with shortwave UV light on a thin layer chromatography plate (Kieselgel 60 F254, EM Separations, Gibbstown, N.J.).

Some oligonucleotides were synthesized without removing the 5'-trityl group (trityl-on) to facilitate reverse-phase HPLC purification. Trityl-on oligonucleotides were dissolved in 3 ml water and centrifuged at 6000 rpm for 20 minutes. The supernatant was filtered through a 0.45 micron syringe filter (Gelman Scientific, Ann Arbor, Mich.) and purified on a 1.5×30 cm glass liquid chromatography column (Spectrum, Houston, Tex.) packed with C-18 μBondapak chromatography matrix (Waters, Franklin, Mass.) using a 600E HPLC (Waters, Franklin, Mass.). The oligonucleotide was Eluted at 5 ml/min with a 40 minute gradient from 14–32% acetonitrile (Baxter, Burdick and Jackson Division, Muskegon, Mich.) in 0.1 M ammonium acetate (J. T. Baker, Phillipsburg, N.J.), followed by 32% acetonitrile for 12 minutes. Peak detection was done at 260 nm using a Dynamax UV-C absorbance detector (Rainin, Emeryville, Calif.).

The HPLC purified trityl-on oligonucleotide was evaporated to dryness and the trityl group was removed by incubation in 5 ml 80% acetic acid (EM Science, Gibbstown, N.J.) for 15 minutes. After evaporating the acetic acid, the oligonucleotide was dissolved in 3 ml 0.3 M NaCl and ethanol precipitated. The precipitate was isolated by centrifugation and precipitated again with ethanol from 3 ml 0.1 M NaCl. The precipitate was isolated by centrifugation and dried on a Savant Speed Vac (Savant, Farmingdale, N.Y.). Quantitation and PAGE analysis were performed as described above for ethanol precipitated oligonucleotides.

Standard phosphoramidite chemistry was applied in the synthesis of oligonucleotides containing methylphosphonate linkages using two Pharmacia Gene Assembler Special DNA synthesizers. One synthesizer was used for the synthesis of phosphorothioate portions of oligonucleotides using P-cyanoethyl phosphoramidites method discussed above. The other synthesizer was used for introduction of methylphosphonate portions. Reagents and synthesis cycles that had been shown advantageous in methylphosphonate synthesis were applied (Hogrefe et al., in *Methods in Molecular Biology*, Vol. 20: *Protocols for Oligonucleotides and Analogs* (Agrawal, ed.) (1993) Humana Press Inc., Totowa, N.J.). For example, 0.1 M methyl phosphonamidites (Glen Research, Sterling, Va.) were activated by 0.25 M ethylthiotetrazole; 12 minute coupling time was used; oxidation with iodine (0.1 M) in tetrahydrofuran/2,6utidine/water (74.75/25/0.25) was applied immediately after the coupling step; dimethylaminopyridine (DMAP) was used for the capping procedure to replace standard N-methylimidazole (NMI). The chemicals were purchased from Aldrich (Milwaukee, Wis.).

The work up procedure was based on a published procedure (Hogrefe et al. (1993) *Nucleic Acids Research* 21:2031–2038). The product was cleaved from the resin by incubation with 1 ml of ethanol/acetonitrile/ammonia hydroxide (45/45/10) for 30 minutes at room temperature. Ethylenediamine (1.0 ml) was then added to the mixture to deprotect at room temperature for 4.5 hours. The resulting solution and two washes of the resin with 1 ml 50/50 acetonitrile/0.1 M triethylammonium bicarbonate (TEAB), pH 8, were pooled and mixed well. The resulting mixture was cooled on ice and neutralized to pH 7 with 6 N HCl in 20/80 acetonitrile/water (4–5 ml), then concentrated to dryness using the Speed Vac concentrator. The resulting solid residue was dissolved in 20 ml of water, and the sample desalted by using a Sep-Pak cartridge. After passing the aqueous solution through the cartridge twice at a rate of 2 ml per minute, the cartridge was washed with 20 ml 0.1 M TEAB and the product Eluted with 4 ml 50% acetonitrile in 0.1 M TEAB at 2 ml per minute. The Eluate was evaporated to dryness by Speed Vac. The crude product was purified by polyacrylamide gel Electrophoresis (PAGE) and desalted using a Sep-Pak cartridge. The oligonucleotide was ethanol precipitated from 0.3 M NaCl, then 0.1 M NaCl. The product was dissolved in 400 µl water and quantified by UV absorbance at 260 nm.

3. E1-Luciferase Gene Fusion Assay

A. Using Stably Transfected Cells

The E1-luciferase fusion pE1Luc6 construct (Roche, Welwyn Garden City, England) consists of 46 nucleotides spanning the translation start site of HPV-6b E1 gene inserted between the cytomegalovirus immediate early gene promoter and luciferase reporter gene in the piasmid pGLori (Hoffman-La Roche, Nutley, N.J.). The E1 target and luciferase gene were subcloned by polymerase chain reaction from this plasmid and the parent plasmid pGLori into the vector pCR-Script (Stratagene, La Jolla, Calif.) and further subdoned into the vector pcDNA3 (Invitrogen, San Diego, Calif.). These constructs (pcDNA3GLori and pcDNA3E1Luc6) were stably transfected using Lipofectamine (GIBCO-BRL, Gaithersburg, Md.) into CHO-K1 cells (American Type Culture Collection (ATCC CCL 60) Rockville, Md.). Several geneticin-resistant, luciferase expressing clones were selected at random for each construct.

Stably transfected CHO cells were seeded into 96 well plates. Cellfectin (GIBCO-BRL, Gaithersburg, Md.) was diluted to a concentration of 4 µg/ml in Optimem serum-free medium (GIBCO-BRL, Gaithersburg, Md.) and 100 µl dispensed into each well of the 96 well plate. Oligonucleotides were diluted to 5 µM or 25 µM in 4 µg/ml Cellfectin in Optimem and 25 µl dispensed into three wells of the 96 well plate. The oligonucleotide was serially diluted in five fold increments down the plate. Four hours after addition of oligonucleotide the wells were aspirated and 100 µl CCM5 medium (Hyclone, Logan, Utah) dispensed into each well. The plates were incubated overnight at 37° C. Cells were washed twice with Dulbecco's phosphat-bufferred saline (PBS) and lysed in 50 µl cell lysis buffer (Analytical Luminescence Laboratory, San Diego, Calif.). Luciferase activity was measured in 20 µl lysate using Analytical Luminescence Laboratory substrates in a MicroLumat LB 96 P luminometer (EG&G Berthold, Nashua, N.H.).

B. Using Transiently Transfected CHO Cells

CHO cells were grown in DMEM complete medium (PMEM+10% fetal calf serum+nonessential amino acids +: sodium pyruvate+L-glutamine+penicillin/streptomycin). $10^4$ CHO cells per well were plated in 96-well white luminometer plates about 15 hr prior to transfection. The medium was removed, and the cells washed twice with DMEM semicomplete medium, (no fetal calf serum or penicillin/streptomycin sulfate).

100 µl of a transfection mix containing E1-luciferase fusion or luciferase reporter plasmids (pE1Luc6 or pGLori, 0.01 to 20 ng/100 µl), oligonucleotide (0.1 nM to 1000 nM), and 8 to 12 µg/ml Lipofectamine (Gibco-BRL, Gaithersburg, Md.) in DMEM semicomplete medium were added. The mixture was incubated for 6 hr at 37° C. 100 µl of DMEM +20% fetal calf serum+2×penicillin/streptomycin sulfate was then added, and the cells incubated for 1 to 7 days.

The cells were washed 2 times with 100 µl phosphate-buffered saline (PBS). Cells were lysed by a −80° C. freeze/thaw cycle in 20 µl reporter lysis buffer (Promega, Madison, Wis.). The luciferase enzyme levels were measured by addition of 100 µl luciferin assay reagent (Promega, Madison, Wis.) using a luminometer (EG&G Berthold Microlumat LB96P, St. Albans, Herts, UK). Each well was counted for 40 sec.

The luciferase enzyme activity data can be plotted by plasmid concentration or oligonucleotide concentration. Specific activity of the antisense oligonucleotides is defined as the percent activity of the oligonucleotide compared to randomer against the E1 luciferase target.

C. Using Transiently Transfected Human Keratinocyte

Neonatal human foreskin keratinocytes (NHEK cells) were transiently transfected with the E1 luciferase fusion plasmid, pE1Luc6, or the control plasmid, pGLori (described above), using Lipofectamine. Antisense oligonucleotides were added to the cells either with the plasmid or after transfection without lipid carrier or before and after transfection without a lipid carrier.

When oligonucleotides of the invention were added with the plasmid, the following method was used. NHEK cells at second passage (strain 2718, Clonetics Corp., San Diego, Calif.) were plated in each well of a 96-well luminometer plate (Dynatech, Billingshurst, West Sussex, UK) at a concentration of $10^4$ cells/well in 100 µl keratinocyte growth medium (KGM) (Clonetics Corp., San Diego, Calif.). The cells were cultured overnight at 37° C. in a humidified $CO_2$ atmosphere. The following transfection mixtures were made for each well in 100 µl keratinocyte basal medium (KBM, (Clonetics Corp., San Diego, Calif.): 1% lipofectamine (Gibco-BRL, Gaithersburg, Md.), 50 ng plasmid DNA and either 0, 0.1, 1, 10 or 100 nM antisense oligonucleotide. Immediately prior to transfection, the cells were washed with KBM. The transfection mixture was placed on the cells for 6 hours at 37° C. This mixture was then removed from the cells. Complete KGM was added and the culture grown for a further 48 hours. Cultures were harvested for reading in the luminometer by removing the medium, washing the cells once with PBS, then adding 50 µl cell lysis buffer (Promega, Madison, Wis.) to each well of the plate, and freezing it at −80° C. Prior to reading the plate in the luminometer (Berthold Microlumat L96P, St. Albans, Herts, UK), it was thawed at room temperature for 30 minutes then 100 µl luciferase substrate buffer (Promega, Madison, Wis.) was added to each well. After a delay of 3 seconds the luciferase activity in each well was measured for 40 seconds.

When oligonucleotides of the invention were added after transfection, the following methodology was used. NHEK cultures were set up in 96 well plates as described above. For these experiments the transfection mixture contained 50 ng plasmid and 1% lipofectamine in KBM. The transfections were carried out as described above. After the 6 hour incubation the transfection mixture was removed, replaced with KBM, then incubated overnight in KGM. The following day the KGM was replaced with KGM containing 0, 0.2, 1.0, 5.0 or 10.0 µM antisense oligonucleotide. Cultures were maintained in this medium for 48 hours before processing for reading in the luminometer as described above. In some cases, cells were treated prior to transient transfection with antisense oligonucleotides diluted in KGM (0–10 µM). They were then transiently transfected and then post-treated with oligonucleotode as described above.

4. Cytotoxicity Assay

The transfection mix containing reporter plasmid, oligonucleotide, and Lipofectamine in DMEM semicomplete medium was assembled as in 3B above. Duplicate aliquots were plated into two microtiter plates: one to determine luciferase expression and one to measure cell viability. The cell viability was measured using the Ceititer 96 Nonradioactive Cell Proliferation/Cytoxicity Assay (Promega, Madison, Wis.). The luciferase activity in Plate 1 was measured as described in B above. To Plate 2, 15 µl MTT dye solution was added to CHO cells in 100 µl DMEM medium. Plates were incubated at 37° C. in humidified 5% $CO_2$ for 4 hours. 100 µl Solubilization/Stop Solution (all reagents included with Promega kit) was added, and the mixture incubated for 1 hour. The optical density of each well was recorded at 570 nm (versus controls).

5. In vivo Testing of HPV-Specific Oligonucleotides

The in vivo method of Kreider et al. (U.S. Pat. No. 4,814,268) is used to determine if the oligonucleotides of the invention are able to inhibit the expression of HPV-specific genes. Briefly, human foreskin grafts were rinsed in Minimum Essential Medium with 800 µg/ml gentamycin (GIBCO-BRL, Gaithersburg, Md.) and then incubated for 1 hour at 37° C. in 1 ml condylomata acuminata (HPV-containing) extract. The extract is prepared from vulvar condylomata which is minced and disrupted in 50 ml PBS at 4° C. with a tissue homogenizer at 25,000 rpm for 30 min. Cell debris is removed by centrifugation. Athymic mice (nu/nu on a BALB/c background) (Harlan Sprague Dawley, Inc., Madison, Wis.) are anesthetized with Nembutal, and the kidneys delivered, one at a time, through dorsal, bilateral, paravertebral, subcostal incisions. The renal capsule is nicked, and foreskin graft is placed in each kidney with toothless forceps. The skin incisions are closed with wound clips, and the mice are given drinking water with trimethoprin (0.01 mg/ml) and sulfamethoxazole (0.05 mg/ml) for the duration of the experiment.

In the experiment, ten mice, each with two grafts (one per kidney), were dosed with 25 mg kg$^{-1}$ day sub-cutaneously for 34 days, then 5 mg kg$^{-1}$ day$^{-1}$ for the remaining 56 days of the experiment, for a total of 90 days exposure to the antisense oligonucleotide HPV1 0×5 Hybrid (SEQ ID NO: 96, Table 1B) which has five 2'-OMe ribonucleotides at the 3'-end. As controls, ten mice, each with two grafts, were treated with saline. Mice were killed by cervical dislocation, the kidneys with the cysts were removed and their size was measured. The standard measure of cyst size used by Kreider is the 'Gross Mean Diameter' (GMD), or the average dimension [i.e., (L +w+h)/3]. The calculated GMD was 2.89±0.23 mm (Table 2) for 10 control animals dosed subcutaneously with saline and 1.62±0.14 mm for the 9 animals dosed with HPV1 0×5 OMe (Table 3). Statistical significance for a drug effect was calculated as p<0.001 according to Student's_test (T=4.59, n=18). Although GMD was used to measure size, a more representative comparison of the difference between the two groups is the ratio of cyst volumes; i.e., the cubes of the two GMDs, or $1.62^3/2.89^3$=the tumor volume in mice treated with HPV1 0×5 OMe compound is 82% lower than the control mice. this is a conservative estimate, as it assumes that the original implanted foreskin chip has no volume at implantation and does not grow at all in the absence of viral infection. Neither of these assumptions are correct. Foreskin chips at implant are~(1 mm×1 mm×skin thickness), and grow slightly even when uninfected as determined in a previous experiment (GMD=1.20±0.363 mm). therefore, subtracting this baseline of uninfected implants, the effect becomes $(1.62-1.20)^3/(2.89-1.20)^3$=a 65-fold (>98%) decrease in cyst size for the antisense oligonucleotide relative to the saline control.

TABLE 2

| Mouse number | Cyst width (mm) | Cyst length (mm) | Cyst height (mm) | Gross mean diameter (mm) | Mean value (mm) |
|---|---|---|---|---|---|
| 1L | 4.2 | 4.0 | 2.7 | 3.6 | |
| 1R | 4.3 | 4.2 | 3.7 | 4.1 | |
| 2L | 3.0 | 2.3 | 1.4 | 2.1 | |
| 2R | 2.8 | 1.3 | 1.0 | 1.5 | |
| 3L | 3.3 | 2.6 | 2.7 | 2.9 | |
| 3R | 3.0 | 2.5 | 1.8 | 2.4 | |
| 4L | 4.5 | 4.5 | 4.5 | 4.5 | |
| 4R | 1.8 | 1.7 | 1.3 | 1.6 | |
| 5L | 5.3 | 4.1 | 3.6 | 4.3 | 2.89 |
| 5R | 5.4 | 4.0 | 3.7 | 4.3 | ±0.23 |
| 6L | 4.4 | 4.4 | 2.8 | 3.8 | |
| 6R | 3.8 | 3.8 | 3.2 | 3.6 | |
| 7L | 1.8 | 2.0 | 1.5 | 1.8 | |
| 7R | 2.4 | 4.2 | 3.1 | 3.1 | |
| 8L | 1.7 | 2.9 | 1.7 | 2.0 | |
| 8R | 2.1 | 2.5 | 1.2 | 1.8 | |
| 9L | 2.1 | 2.5 | 1.7 | 2.1 | |
| 9R | 2.3 | 2.3 | 1.3 | 1.9 | |
| 10L | 4.0 | 4.2 | 3.6 | 3.9 | |
| 10R | 2.7 | 3.0 | 1.9 | 2.5 | |

TABLE 3

HPV1 0x5 OMe (dosed as mentioned above)

| Mouse number | Cyst width (mm) | Cyst length (mm) | Cyst height (mm) | Gross mean diameter (mm) | Mean value (mm) |
|---|---|---|---|---|---|
| 1L | 3.0 | 2.7 | 2.0 | 2.5 | |
| 1R | 2.1 | 2.6 | 2.0 | 2.2 | |
| 2L | 1.0 | 1.3 | 0.7 | 1.0 | |
| 2R | 2.1 | 3.3 | 2.1 | 2.4 | |
| 3L | 1.6 | 2.2 | 1.5 | 1.7 | |
| 3R | 2.8 | 2.8 | 2.5 | 2.7 | |

TABLE 3-continued

HPV1 Ox5 OMe (dosed as mentioned above)

| Mouse number | Cyst width (mm) | Cyst length (mm) | Cyst height (mm) | Gross mean diameter (mm) | Mean value (mm) |
|---|---|---|---|---|---|
| 4L | 1.5 | 2.1 | 1.3 | 1.6 | |
| 4R | 1.5 | 0.9 | 0.8 | 1.0 | 1.62 |
| 6L | 2.0 | 2.0 | 1.1 | 1.6 | ±0.14 |
| 6R | 1.3 | 1.5 | 0.9 | 1.2 | |
| 7L | 2.0 | 1.5 | 0.9 | 1.4 | |
| 7R | 1.5 | 0.9 | 0.8 | 1.0 | |
| 8L | 3.1 | 2.3 | 1.7 | 2.3 | |
| 8R | 2.4 | 2.4 | 1.7 | 2.1 | |
| 9L | 1.3 | 1.2 | 0.8 | 1.1 | |
| 9R | 1.5 | 1.1 | 0.6 | 1.0 | |
| 10L | 1.6 | 1.3 | 1.0 | 1.3 | |
| 10R | 1.4 | 1.1 | 1.7 | 1.0 | |

Moreover, after determination of the cyst size the kidneys are fixed in neutral-buffered formalin, embedded in paraffin, sectioned at 6 microns and stained with hematoxylin and eosin. Cohort sections are deparaffinized and incubated with antibody raised against disrupted bovine papillomavirus (Kakopatts, Accurate Chemical & Scientific Corp., Westbury, N.Y.) for the demonstration by the immunoperoxidase technique of the group-specific antigen (GSA). (See, Jensen et al., (1980) *J. Natl. Cancer Inst.* 64:495–500; and Kurman, et al. (1983) *Am. J. Surg. Path.* 7:39–52). GSA is a capsid antigen common to most papillomaviruses. Positive controls consist of canine papillomas or human vulvar condylomata. Negative controls are normal human skin.

6. Studies of CHO-K1 Cells Stably Transfected With The Full Length HPV E1 Gene

The full length E1 gene is subcloned from the plasmid pE16B1 (Roche Welwyn Garden City, UK) (SEQ ID NO:40) by polymerase chain reaction into the vector pcDNA3 (Invitrogen, San Diego, Calif.). This is transfected into CHO-K1 cells, and geneticinresistant (GIBCO-BRL, Gaithersburg, Md.) clones isolated. These clones are tested by western blot for expression of E1 protein. Positive clones are used for antisense oligonucleotide assays, efficacy being measured by western blots for translation inhibition, and northern blots and ribonuclease protection studies for RNA depletion and RNase H cleavage products. In addition E1-expressing cells are transiently transfected with pHPVE2 and pgLori to assay for inhibition of HPV DNA replication.

7. E1 RNA Dot Blot Assay

To confirm the validity of the E1-luciferase enzyme assay, which measured E1-luciferase expression as a surrogate marker for the expression of the actual viral E1 target, E1 mRNA levels were measured in CHO cells using an assay system similar to that described by Plumpton et al. (*Biotechnol.* (1995) 31:1210–1214).

CHO celsl were transfected with pE16B1(SEQ ID NO:40), a plasmid expressing the entire open reading frame of E1, with 103 nt of 5' untranslated region. Cells were then treated with either a placebo or 100 nM of HPV1, HPV9 (with three mismatches), or Randomer phosphorothioate compounds. Another set of CHO cells was treated with the same antisense compounds but not transfected with expression plasmid, and finally RNA was isolated from all eight CHO samples. Total RNA was hybridized to labelled oligonucleotide probes for either the E1 message or an actin control, and message levels of each transcript were measured by quantification of label intensity on a phosphorimager.

Cells transfected with E1 construct but treated only with placebo expressed high levels of E1 message. Cells treated with the randomer control oligonucleotide expressed identical high levels of E1. However, cells treated with the mismatched HPV29 reduced levels of E1 expression by −40%. Finally, cells treated with HPV1, a perfect match to the viral gene target, reduced E1 messenger RNA by −80%. In contrast, control CHO cells not transfected with E1 construct showed no effects of antisense treatment. In addition, all eight CHO RHA samples showed similar levels of actin RNA, indicating that antisense effects were specific to E1 gene expression. This work suggests that oligonucleotides targeting human papillomavirus E1 gene expression direction reduce mRNA levels in the cell, and confirms that antisense activity in the E1-luciferase surrogate assay used for routine screening correlates with direct measurements of E1 RNA levels.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

We claim:

1. A synthetic oligonucleotide comprising a sequence selected from the group consisting of SEQ ID NOS: 41, 42, 43, 44, 45, 46, 47, 48, 49, and 96 wherein the oligonucleotide comprises no more than about 30 nucleotides.

2. The oligonucleotide of claim 1 which is modified.

3. The oligonucleotide of claim 2 wherein the modification is as set forth in Table B for SEQ ID NOS: 41–49 and 96.

4. The oligonucleotide according to claim 1 which comprises at least one deoxyribonucleotide.

5. The oligonucleotide of claim 1 which comprises at least one ribonucleotide.

6. The oligonucleotide according to claim 4 which additionally comprises at least one ribonucleotide.

7. The oligonucleotide according to claim 6 wherein an oligodeoxyriboucleotide region is interposed between two oligoribonucleotide regions, or the inverted configuration thereof.

8. The oligonucleotide according to claim 5, wherein the ribonucleotide is a 2'-O-methyl ribonucleotide.

9. The oligonucleotide according to claim 6, wherein the ribonucleotide is a 2'-O-methyl ribonucleotide.

10. The oligonucleotide according to claim 7, wherein the ribonucleotide is a 2'-O-methyl ribonucleotide.

11. The oligonucleotide according to claim 6 which comprises at least one 2'-O-methyl ribonucleotide at the 3' end of the oligonudeotide.

12. The oligonucleotide according to claim 11 which further comprises at least one 2'-O-methyl ribonucleotide at the 5' end of the oligonucleotide.

13. The oligonucleotide according to claim 1, wherein the oligonucleotide is modified and comprises at least one internucleotide linkage selected from the group consisting of alkylphosphonate, phosphorothioate, phosphorodithioate, alkylphosphonothioate, phosphoramidate, carbamate, carbonate, phosphate triester, acetamidate, carboxymethyl ester.

14. The oligonucleotide according to claim 13, wherein the alkylphosphonate is a methylphosphonate.

15. The oligonucleotide according to claim 13, wherein the phosphoramidate is an n-butyl phosphoramidate.

16. The oligonucleofide according to claim 14 comprising at least one phosphorothioate internucleotide linkage.

17. The oligonucleotide according to claim 15 comprising at least one phosphorothioate internudeotide linkage.

18. The oligonucleotide according to claim 13 wherein all internucleotide linkages in the oligonucleotide are phosphorothioate internucleotide linkages.

19. The oligonucleotide according to claim 13, comprising a backbone comprising a phosphorothioate region interposed between nonionic internucleotide linkage flanking regions, or the inverted configuration thereof.

20. The oligonucleotide according to claim 14, comprising a backbone comprising a phosphorothioate region interposed between nonionic internucleotide linkage flanking regions, or the inverted configuration thereof.

21. The oligonucleotide according to claim 15, comprising a backbone comprising a phosphorothioate region interposed between nonionic internucleotide linkage flanking regions, or the inverted configuration thereof.

22. The oligonucleotide according to claim 13 which comprises a backbone comprising an oligodeoxyribonucleotide region interposed between 2'O-substituted or unsubstituted ribonucleotide flanking regions, which backbone further comprises at least one n-butyl phosphoramidate or at least one methylphosphonate internucleotide linkage.

23. The oligonucleotide of claim 1 wherein at least one nucleoside is substituted by inosine or wherein at least one deoxycytosine is substituted by 5-methyl deoxycytosine.

24. The oligonucleotide according to claim 23 comprising two inosine or two 5-methyl deoxycytosine nucleosides.

25. A synthetic and modified oligonucleotide comprising a target hybridizing region of at least 15 nucleotides filly complementary to a nucleic acid sequence spanning the translational start site of human papillomavirus gene E1, wherein the oligonucleotide firther comprises a self-complementary region comprising at least one of the following modifications: a self-stabilizing loop, a nicked dumbbell, a closed dumbbell, a 2' cap, a 3' cap, a 5' cap, and non-nucleoside linker.

26. A synthetic and modified oligonucleotide comprising a target hybridizing region fully complementary to a nucleic acid sequence spanning the translational start site of human papillomavirus gene E1, wherein the oligonucleotide further comprises at most about 32 nucleotides and comprises a sequence selected from the group consisting of SEQ ID NOS: 41–49 and 96 as given in Table 1B and wherein the oligonucleotide comprises the intemucleotide linkage composition and modifications as set forth in Table 1B for SEQ ID NOS: 41–49 and 96.

27. An oligonucleotide sequence consisting of a sequence selected from the group consisting of: SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49 and SEQ ID NO: 96.

28. The synthetic and modified oligonucleotide of claim 25, wherein the oligonucleotide comprises an addition to the internucleoside phosphate linkage of the oligonucleotide.

29. The synthetic and modified oligonucleotide of claim 25, wherein the oligonucleotide is modified by oxidation, oxidation/reduction, or xtidative/reductive amination.

30. The oligonucleotide of claim 25 wherein the target hybridizing region is selected from the group consisting of SEQ ID NOS: 41–49 and 96 as set forth in Table 1B.

* * * * *

SEQUENCE LISTING (1) GENERAL INFORMATION:

(iii) NUMBER OF SEQUENCES: 130

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:1:

GTACCTGAAT CGTCCGCCAT                                                   20

(2) INFORMATION FOR SEQ ID NO:2:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:2:

CATCGTTGTT AGGTCTTCGG                                                   20

(2) INFORMATION FOR SEQ ID NO:3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:3:

TCGTCCGCCA TCGTTGTTAG                                                   20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:4:

CCGCCATCGT TGTTAGGTCT                                                   20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:5:

TGAATCGTCC GCCATCGTTG                                                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:6:

CATTTTCTGT ACCTGAATCG                                                    20

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:7:

GTACCTGAAT CGTCCGCCAT CGTTGTTA                                           28

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:8:

GTACCTGAAT CGTCCGCCAT CGTTG                                              25

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:9:

TTTTCTGTAC CTGAATCGTC                                                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:10:

CCCCTCATTT TCTGTACCTG                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:11:

ACCCAGACCC CTCATTTTCT                                    20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:12:

GGGTGTCCGC CTCCTGCCTG                                    20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:13:

CGTTTTAGGT CCTGCACAGT                                    20

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:14:

GCCTCGGCTA TAGTGTTTAT                                              20

(2) INFORMATION FOR SEQ ID NO:15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:15:

CGTCGCTTTA CCTTTTTTGG                                              20

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:16:

CCAGACCCCT CATTTTCTGT                                              20

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:17:

ATAAACCATC CTGTACACCC                                              20

(2) INFORMATION FOR SEQ ID NO:18:

(i) SEQUENCE CHARACTERISTICS:
            (A) LENGTH: 17 base pairs
            (B) TYPE: nucleic acid (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:18:

CCTGAATCGT CCGCCAT                                                          17

(2) INFORMATION FOR SEQ ID NO:19:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:19:

GTACCTGAAT CGTCCGCCA                                                        19

(2) INFORMATION FOR SEQ ID NO:20:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:20:

TACCTGAATC GTCCGCCAT                                                        19

(2) INFORMATION FOR SEQ ID NO:21:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:21:

ACCTGAATCG TCCGCCAT                                                         18

(2) INFORMATION FOR SEQ ID NO:22:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:22:

CTGAATCGTC CGCCAT                                              16

(2) INFORMATION FOR SEQ ID NO:23:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:23:

GTACCTGAAT CGTCC                                               15

(2) INFORMATION FOR SEQ ID NO:24:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:24:

GTACCTGAAT CGTCCG                                              16

(2) INFORMATION FOR SEQ ID NO:25:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:25:

GTACCTGAAT CGTCCGC                                             17

(2) INFORMATION FOR SEQ ID NO:26:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:26:

GTACCTGAAT CGTCCGCC                                                              18

(2) INFORMATION FOR SEQ ID NO:27:

(i) SEQUENCE CHARACTERISTICS:
              (A) LENGTH: 15 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:27:

TGAATCGTCC GCCAT                                                                 15

(2) INFORMATION FOR SEQ ID NO:28:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:28:

GTACCTGAAT CGTCCGCCAT CGTTGTTAGG                                                  30

(2) INFORMATION FOR SEQ ID NO:29:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:29:

TCTTTTTTTT TTTTCTGTAC CTGAATCGTC                                                  30

(2) INFORMATION FOR SEQ ID NO:30:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:30:

ACCCAGACCC CTCATTTTCT TTTTTCTTTT                                              30

(2) INFORMATION FOR SEQ ID NO:31:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:31:

GTACCTAAAT CGTCCGCCAT                                                         20

(2) INFORMATION FOR SEQ ID NO:32:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:32:

GTACCTAAAT CATCCGCCAT                                                         20

(2) INFORMATION FOR SEQ ID NO:33:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:33:

GTACCTAAAT CATCCACCAT                                                         20

(2) INFORMATION FOR SEQ ID NO:34:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:34:

ATACCTAAAT CATCCACCAT                                                         20

(2) INFORMATION FOR SEQ ID NO:35:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:35:

GTGCCAGAGT CGTCCGCCAT   20

(2) INFORMATION FOR SEQ ID NO:36:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:36:

GTACCTNAAT CATCCGCCAT   20

(2) INFORMATION FOR SEQ ID NO:37:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:37:

GTACCTAAAT CNTCCGCCAT   20

(2) INFORMATION FOR SEQ ID NO:38:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:38:

GTACCTNAAT CNTCCGCCAT   20

(2) INFORMATION FOR SEQ ID NO:39:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:39:

ATGTTTTTGG CGTCTTCCAT                    20

(2) INFORMATION FOR SEQ ID NO:40:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:40:

TCGAAGCTCA GATCCGAAGA CCTAACAACG ATGGCGGACG ATTCAGGTAC AGAAAATGAG    60

GGGTCTGGGT GTACAGGATG GTTTATGGTA GAAGCTATAG TGCAACA                 107

(2) INFORMATION FOR SEQ ID NO:41:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:41:

GTACCTGAAT CGTCCGCCAT NATGGC              26

(2) INFORMATION FOR SEQ ID NO:42:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:42:

GTACCTGAAT CGTCCGCCAT TTTTATGGC           29

(2) INFORMATION FOR SEQ ID NO:43:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:43:

GTACCTGAAT CGTCCGCCAT TTTATGGC                28

(2) INFORMATION FOR SEQ ID NO:44:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:44:

GTACCTGAAT CGTCCGCCAT TTATGGC                 27

(2) INFORMATION FOR SEQ ID NO:45:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:45:

GTACCTGAAT CGTCCGCCAT TATGGC                  26

(2) INFORMATION FOR SEQ ID NO:46:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:46:

GTACCTGAAT CGTCCGCCAT ATGGC 25

(2) INFORMATION FOR SEQ ID NO:47:

(i) SEQUENCE CHARACTERISTICS:
       (A) LENGTH: 24 base pairs
       (B) TYPE: nucleic acid

```
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:47:

GTACCTGAAT CGTCCGCCAT TGGC    24

(2) INFORMATION FOR SEQ ID NO:48:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:48:

GTACCTGAAT CGTCCGCCAT GGACG    25

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:49:

GTACCTGAAT CGTCCGCCAT GGAC    24

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:50:

GTACCTGAAT CGTCCGCCAT GGA    23

(2) INFORMATION FOR SEQ ID NO:51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

(ii) MOLECULE TYPE: DNA (iii) HYPOTHETICAL: NO (iv) ANTI-SENSE: YES/NO (xi) SEQUENCE DESCRIPTION: SEQ ID NO:51:

GTACCTGAAT CGTCCGCCAT TCA    23

(2) INFORMATION FOR SEQ ID NO:52:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:52:

GTACCTGAAT CGTCCGCCAT GGTAC 25

(2) INFORMATION FOR SEQ ID NO:53:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:53:

GATGGTACCT GAATCGTCCG CCATC 25

(2) INFORMATION FOR SEQ ID NO:54:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:54:

CTGAATCGTC CGCCATC         17

(2) INFORMATION FOR SEQ ID NO:55:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:55:

CTGAATCGTC CGCCATCNGA TGG     23

(2) INFORMATION FOR SEQ ID NO:56:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:56:

CTGAATCGTC CGCCATCTTT TGATGG                 26

(2) INFORMATION FOR SEQ ID NO:57:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:57:

CTGAATCGTC CGCCATCGGA C     21

(2) INFORMATION FOR SEQ ID NO:58:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:58:

CTGAATCGTC CGCCATCGGA    20

(2) INFORMATION FOR SEQ ID NO:59:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:59:

CTGAATCGTC CGCCATCGG          19

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:60:

CTGAATCGTC CGCCATCGAT T     21

(2) INFORMATION FOR SEQ ID NO:61:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:61:

CCTGAATCGT CCGCCATCAG G      21

(2) INFORMATION FOR SEQ ID NO:62:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:62:

CTGAATCGTC CGCCATCAG          19

(2) INFORMATION FOR SEQ ID NO:63:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES/NO (xi) SEQUENCE DESCRIPTION: SEQ ID NO:63:

CTGAATCGTC CGCCATCUGG CCUUUUGGCC A          31

(2) INFORMATION FOR SEQ ID NO:64:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES/NO (xi) SEQUENCE DESCRIPTION: SEQ ID NO:64:

CTGAATCGTC CGCCATCUGG CCNGGCCA                28

(2) INFORMATION FOR SEQ ID NO:65:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:65:

CTGAATCGTC CGCCATCTGG CCTTTTGGCC A            31

(2) INFORMATION FOR SEQ ID NO:66:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:66:

CTGAATCGTC CGCCATCTGG CCNGGCCA                28

(2) INFORMATION FOR SEQ ID NO:67:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:67:

GGCCATTTTT GGCCCTGAAT CGTCCGCCAT C            31

(2) INFORMATION FOR SEQ ID NO:68:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:68:

GGCCANTGGC CCTGAATCGT CCGCCATC                28

(2) INFORMATION FOR SEQ ID NO:69:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:69:

TGGCCCTGAA TCGTCCGCCA TCTTTTGGCC A            31

(2) INFORMATION FOR SEQ ID NO:70:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:70:

TGGCCCTGAA TCGTCCGCCA TCNGGCCA                28

(2) INFORMATION FOR SEQ ID NO:71:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:71:

GGCCATTTTC TGAATCGTCC GCCATCTGGC C            31

(2) INFORMATION FOR SEQ ID NO:72:

(i) SEQUENCE CHARACTERISTICS:
        (A) LENGTH: 28 base pairs (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:72:

GGCCANCTGA ATCGTCCGCC ATCTGGCC                28

(2) INFORMATION FOR SEQ ID NO:73:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:73:

GGCCANCTGA ATCGTCCGCC ATCNTGGCC               29

(2) INFORMATION FOR SEQ ID NO:74:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:74:

CTGAATCGTC CGCCATCGTT  20

(2) INFORMATION FOR SEQ ID NO:75:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:75:

CTGAATCGTC CGCCATCGTT TGGCG 25

(2) INFORMATION FOR SEQ ID NO:76:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:76:

CTGAATCGTC CGCCATCGTT G        21

(2) INFORMATION FOR SEQ ID NO:77:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:77:

CTGAATCGTC CGCCATCGTT GATGG 25

(2) INFORMATION FOR SEQ ID NO:78:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:78:

CTGAATCGTC CGCCATCGTT GATGGC                    26

(2) INFORMATION FOR SEQ ID NO:79:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:79:

CTGAATCGTC CGCCATCGTT GATGGCG                   27

(2) INFORMATION FOR SEQ ID NO:80:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:80:

GTACCTGAAT CGTCCGCCAT TNTATGGC            28

(2) INFORMATION FOR SEQ ID NO:81:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES/NO (xi) SEQUENCE DESCRIPTION: SEQ ID NO:81:

GTACCTGAAT CGTCCGCCAT UUUAUGGC            28

(2) INFORMATION FOR SEQ ID NO:82:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES/NO (xi) SEQUENCE DESCRIPTION: SEQ ID NO:82:

GTACCTGAAT CGTCCGCCAU UUUATGGC            28

(2) INFORMATION FOR SEQ ID NO:83:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES/NO (xi) SEQUENCE DESCRIPTION: SEQ ID NO:83:

GTACCTGAAT CGTCCGCCAU UUUAUGGC            28

(2) INFORMATION FOR SEQ ID NO:84:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:84:

ATTCAGGTAC CTGAATCGTC CGCCATCGGA CG          32

(2) INFORMATION FOR SEQ ID NO:85:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:85:

ATTCAGTACC TGAATCGTCC GCCATGGACG          30

(2) INFORMATION FOR SEQ ID NO:86:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:86:

GATTCAGTAC CTGAATCGTC CGCCATGGAC          30

(2) INFORMATION FOR SEQ ID NO:87:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:87:

GATTCAGGTA CCTGAATCGT CCGCCATCGG AC          32

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:88:

GTACCTGAAU CGTCCGCCAT    20

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:89:

GTACCTGAAU CGUCCGCCAT    20

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:90:

GTACCTGAAU CGUCCGCCAT    20

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:91:

GTACCUGAAU CGTCCGCCAT    20

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:92:

GTACCTGAAT CGUCCGCCAT    20

(2) INFORMATION FOR SEQ ID NO:93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:93:

GTACCTGAAU CGUCCGCCAT  20

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (ix) FEATURE:
        (A) NAME/KEY: misc_feature
        (B) LOCATION: 1..20
        (D) OTHER INFORMATION: /note= "With respect to Sequence ID
            Number 94 only, N is used to describe the base INOSINE
            as defined in the specification."

(xi) SEQUENCE DESCRIPTION: SEQ ID NO:94:

GTACCTGAAT CNTCCNCCAT                                            20

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:95:

GUACCTGAAT CGTCCGCCAU                                            20

(2) INFORMATION FOR SEQ ID NO:96:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:96:

GTACCTGAAT CGTCCGCCAU                                              20

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:97:

GUACCTGAAT CGTCCGCCAU                                              20

(2) INFORMATION FOR SEQ ID NO:98:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:98:

GUACCTGAAT CGTCCGCCAU                                              20

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:99:

GTACCTGAAT CGTCCGCCAU                                              20

(2) INFORMATION FOR SEQ ID NO:100:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:100:

GTACCTGAAT CGTCCGCCAU                                              20

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:101:

GTACCTGAAT CGTCCGCCAU                                             20

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:102:

GTACCTGAAT CGTCCGCCAU                                             20

(2) INFORMATION FOR SEQ ID NO:103:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:103:

CUGAATCGTC CGCCAUC                                                17

(2) INFORMATION FOR SEQ ID NO:104:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:104:

CTGAATCGTC CGCCAUC                                                17

(2) INFORMATION FOR SEQ ID NO:105:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:105:

CUGAATCGTC CGCCAUC                                                17

(2) INFORMATION FOR SEQ ID NO:106:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:106:

CTGAATCGTC CGCCAUC                                                17

(2) INFORMATION FOR SEQ ID NO:107:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:107:

CUGAATCGTC CGCCAUC                                                17

(2) INFORMATION FOR SEQ ID NO:108:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:108:

CTGAATCGTC CGCCAUC                                                17

(2) INFORMATION FOR SEQ ID NO:109:

(i) SEQUENCE CHARACTERISTICS:
        (A) LENGTH: 17 base pairs
        (B) TYPE: nucleic acid

```
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:109:

CUGAATCGTC CGCCAUC                                                    17

(2) INFORMATION FOR SEQ ID NO:110:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:110:

GUACCTGAAT CGUCCG                                                     16

(2) INFORMATION FOR SEQ ID NO:111:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:111:

GTACCTGAAT CGUCCG                                                     16

(2) INFORMATION FOR SEQ ID NO:112:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:112:

ATCGTCCGCC AT                                                         12

(2) INFORMATION FOR SEQ ID NO:113:

(i) SEQUENCE CHARACTERISTICS:
        (A) LENGTH: 12 base pairs
        (B) TYPE: nucleic acid
        (C) STRANDEDNESS: single
        (D) TOPOLOGY: linear
```

(ii) MOLECULE TYPE: cDNA/RNA (iii) HYPOTHETICAL: NO (iv) ANTI-SENSE: YES (xi) SEQUENCE DESCRIPTION: SEQ ID NO:113:

AUCGTCCGCC AU                                                                  12

(2) INFORMATION FOR SEQ ID NO:114:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: cDNA/RNA (iii) HYPOTHETICAL: NO (iv) ANTI-SENSE: YES (xi) SEQUENCE DESCRIPTION: SEQ ID NO:114:

ATCGTCCGCC AU                                                                  12

(2) INFORMATION FOR SEQ ID NO:115:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:115:

NCTGAATCGT CCGCCATC                                                            18

(2) INFORMATION FOR SEQ ID NO:116:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:116:

TTTCTGTACC TGAATCGTCC                                                          20

(2) INFORMATION FOR SEQ ID NO:117:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:117:

TTCTGTACCT GAATCGTCCG                                          20

(2) INFORMATION FOR SEQ ID NO:118:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:118:

TCTGTACCTG AATCGTCCGC                                          20

(2) INFORMATION FOR SEQ ID NO:119:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:119:

CTGTACCTGA ATCGTCCGCC                                          20

(2) INFORMATION FOR SEQ ID NO:120:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:120:

TGTACCTGAA TCGTCCGCCA                                          20

(2) INFORMATION FOR SEQ ID NO:121:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (iii) HYPOTHETICAL: NO (iv) ANTI-SENSE: YES

```
    (xi) SEQUENCE DESCRIPTION: SEQ ID NO:121:

TACCTGAATC GTCCGCCATC                                                    20

(2) INFORMATION FOR SEQ ID NO:122:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:122:

GTACCTGAAT CGTCCGCCAT CCTT                                               24

(2) INFORMATION FOR SEQ ID NO:123:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:123:

TACCGCCTGC TAAGTCCATG                                                    20

(2) INFORMATION FOR SEQ ID NO:124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:124:

ATGGCGGACG ATTCAGGTAC                                                    20

(2) INFORMATION FOR SEQ ID NO:125:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:125:

GTACCTGAAT CG                                                            12
```

(2) INFORMATION FOR SEQ ID NO:126:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:126:

GTACCTGAAT CGT          13

(2) INFORMATION FOR SEQ ID NO:127:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:127:

GTACCTGAAT CGTC         14

(2) INFORMATION FOR SEQ ID NO:128:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:128:

AATCGTCCGC CAT          13

(2) INFORMATION FOR SEQ ID NO:129:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:129:

GAATCGTCCG CCAT         14

(2) INFORMATION FOR SEQ ID NO:130:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES/NO (xi) SEQUENCE DESCRIPTION: SEQ ID NO:130:

GTACCTGAAT CGTCCGCCAT C                                              21
```